United States Patent
Frey

(10) Patent No.: US 8,870,889 B2
(45) Date of Patent: **\*Oct. 28, 2014**

(54) PATIENT MATCHING SURGICAL GUIDE AND METHOD FOR USING THE SAME

(71) Applicant: George Frey, Englewood, CO (US)

(72) Inventor: George Frey, Englewood, CO (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/841,069

(22) Filed: Mar. 15, 2013

(65) Prior Publication Data

US 2013/0218163 A1   Aug. 22, 2013

Related U.S. Application Data

(63) Continuation-in-part of application No. 13/172,683, filed on Jun. 29, 2011, now Pat. No. 8,758,357.

(60) Provisional application No. 61/359,710, filed on Jun. 29, 2010, provisional application No. 61/393,695, filed on Oct. 15, 2010, provisional application No. 61/625,559, filed on Apr. 17, 2012.

(51) Int. Cl.
*A61B 17/58* (2006.01)
*A61B 17/15* (2006.01)
(Continued)

(52) U.S. Cl.
CPC .............. *A61B 17/151* (2013.01); *G06F 17/50* (2013.01); *A61B 17/00* (2013.01);
(Continued)

(58) Field of Classification Search
USPC ............ 600/407–469; 606/79, 88–96; 602/26
See application file for complete search history.

(56) References Cited

U.S. PATENT DOCUMENTS 3,151,392 A   10/1964   Chambers
5,201,734 A    4/1993   Cozad et al.
(Continued)

FOREIGN PATENT DOCUMENTS

CN   201275138   7/2009
CN   201404283   2/2010
(Continued)

OTHER PUBLICATIONS

U.S. Appl. No. 29/476,699, filed Dec. 16, 2013, Frey et al.
(Continued)

*Primary Examiner* — Sanjay Cattungal
(74) *Attorney, Agent, or Firm* — Sheridan Ross P.C.

(57) ABSTRACT

A system and method for developing customized apparatus for use in one or more surgical procedures is disclosed. The system and method incorporates a patient's unique anatomical features or morphology, which may be derived from capturing MRI data or CT data, to fabricate at least one custom apparatus. According to a preferred embodiment, the customized apparatus comprises a plurality of complementary surfaces based on a plurality of data points from the MRI or CT data. Thus, each apparatus may be matched in duplicate and oriented around the patient's own anatomy, and may further provide any desired axial alignments or insertional trajectories. In an alternate embodiment, the apparatus may further be aligned and/or matched with at least one other apparatus used during the surgical procedure.

16 Claims, 37 Drawing Sheets

(51) Int. Cl.

| | | |
|---|---|---|
| *G06F 17/50* | (2006.01) | |
| *A61B 17/00* | (2006.01) | |
| *A61B 17/17* | (2006.01) | |
| *A61B 17/16* | (2006.01) | |
| *A61B 17/70* | (2006.01) | |
| *A61B 19/00* | (2006.01) | |
| *G09B 23/30* | (2006.01) | |
| *A61F 2/30* | (2006.01) | |
| *A61F 2/44* | (2006.01) | |
| *A61F 2/46* | (2006.01) | |
| *A61B 17/56* | (2006.01) | |
| *A61B 5/0488* | (2006.01) | |
| *A61B 5/00* | (2006.01) | |

(52) U.S. Cl.
CPC ............ *A61B 17/1757* (2013.01); *A61B 17/15* (2013.01); *A61B 17/1671* (2013.01); *A61B 17/70* (2013.01); *A61B 19/50* (2013.01); *G09B 23/30* (2013.01); *A61F 2/30965* (2013.01); *A61F 2/4405* (2013.01); *A61F 2/4611* (2013.01); *A61B 2017/568* (2013.01); *A61B 2019/508* (2013.01); *A61F 2002/3095* (2013.01); *A61F 2002/30952* (2013.01); *A61F 2002/4687* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01); *A61B 5/0488* (2013.01); *A61B 5/4893* (2013.01)
USPC ............................................ 606/96; 600/424

(56) References Cited

U.S. PATENT DOCUMENTS

| | | | |
|---|---|---|---|
| D359,557 S | 6/1995 | Hayes | |
| D403,066 S | 12/1998 | DeFonzo | |
| D412,032 S | 7/1999 | Mikula-Curtis et al. | |
| D420,132 S | 2/2000 | Bucholz et al. | |
| D428,989 S | 8/2000 | Segermark et al. | |
| 6,711,432 B1* | 3/2004 | Krause et al. ................ | 600/427 |
| 6,755,839 B2 | 6/2004 | Van Hoeck et al. | |
| D532,515 S | 11/2006 | Buttler et al. | |
| D533,664 S | 12/2006 | Buttler et al. | |
| D606,195 S | 12/2009 | Eisen et al. | |
| 7,658,610 B2 | 2/2010 | Knopp | |
| D618,796 S | 6/2010 | Cantu et al. | |
| 7,844,356 B2 | 11/2010 | Matov et al. | |
| 7,957,824 B2 | 6/2011 | Boronvinskih et al. | |
| 8,206,396 B2* | 6/2012 | Trabish ........................ | 606/89 |
| 8,257,083 B2* | 9/2012 | Berckmans et al. .......... | 433/213 |
| D669,176 S | 10/2012 | Frey | |
| D672,038 S | 12/2012 | Frey | |
| 8,357,111 B2* | 1/2013 | Caillouette et al. ............ | 602/26 |
| 8,419,740 B2* | 4/2013 | Aram et al. .................... | 606/88 |
| 2004/0097925 A1 | 5/2004 | Boehm et al. | |
| 2006/0084986 A1 | 4/2006 | Grinberg et al. | |
| 2006/0149375 A1 | 7/2006 | Yuan et al. | |
| 2006/0241385 A1 | 10/2006 | Dietz | |
| 2007/0288030 A1 | 12/2007 | Metzger et al. | |
| 2008/0114370 A1* | 5/2008 | Schoenefeld ................. | 606/96 |
| 2008/0161815 A1 | 7/2008 | Schoenefeld et al. | |
| 2008/0183214 A1 | 7/2008 | Copp et al. | |
| 2008/0257363 A1 | 10/2008 | Schoenefeld et al. | |
| 2008/0275452 A1 | 11/2008 | Lang et al. | |
| 2008/0312659 A1 | 12/2008 | Metzger et al. | |
| 2008/0319491 A1 | 12/2008 | Schoenefeld | |
| 2009/0087276 A1 | 4/2009 | Rose | |
| 2009/0088674 A1* | 4/2009 | Caillouette et al. ............ | 602/26 |
| 2009/0088761 A1* | 4/2009 | Roose et al. ................... | 606/87 |
| 2009/0088763 A1* | 4/2009 | Aram et al. .................... | 606/88 |
| 2009/0093816 A1* | 4/2009 | Roose et al. ................... | 606/87 |
| 2009/0099567 A1* | 4/2009 | Zajac ............................ | 606/79 |
| 2009/0110498 A1 | 4/2009 | Park | |
| 2009/0138020 A1 | 5/2009 | Park et al. | |
| 2009/0187194 A1 | 7/2009 | Hamada | |
| 2009/0198277 A1 | 8/2009 | Gordon et al. | |
| 2009/0254093 A1 | 10/2009 | White et al. | |
| 2009/0270868 A1 | 10/2009 | Park et al. | |
| 2010/0049195 A1 | 2/2010 | Park et al. | |
| 2010/0087829 A1 | 4/2010 | Metzger et al. | |
| 2010/0100193 A1 | 4/2010 | White | |
| 2010/0152782 A1 | 6/2010 | Stone et al. | |
| 2010/0191244 A1 | 7/2010 | White et al. | |
| 2010/0217270 A1 | 8/2010 | Polinski et al. | |
| 2010/0217336 A1 | 8/2010 | Crawford et al. | |
| 2010/0305700 A1 | 12/2010 | Ben-Arye et al. | |
| 2010/0324692 A1 | 12/2010 | Uthgenannt et al. | |
| 2011/0015636 A1 | 1/2011 | Katrana et al. | |
| 2011/0015639 A1 | 1/2011 | Metzger et al. | |
| 2011/0046735 A1 | 2/2011 | Metzger et al. | |
| 2011/0054478 A1 | 3/2011 | Vanasse et al. | |
| 2011/0071533 A1 | 3/2011 | Metzger et al. | |
| 2011/0093023 A1 | 4/2011 | Lee et al. | |
| 2011/0093086 A1 | 4/2011 | Witt et al. | |
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0184419 A1 | 7/2011 | Meridew et al. | |
| 2011/0184526 A1 | 7/2011 | White et al. | |
| 2011/0190899 A1 | 8/2011 | Pierce et al. | |
| 2011/0213376 A1 | 9/2011 | Maxson et al. | |
| 2011/0218545 A1 | 9/2011 | Catanzarite et al. | |
| 2011/0224674 A1 | 9/2011 | White et al. | |
| 2011/0288433 A1 | 11/2011 | Kelleher et al. | |
| 2011/0319745 A1* | 12/2011 | Frey ............................... | 600/407 |
| 2012/0041445 A1* | 2/2012 | Roose et al. .................... | 606/96 |
| 2012/0130434 A1 | 5/2012 | Stemniski | |
| 2012/0179259 A1 | 7/2012 | McDonough et al. | |
| 2012/0215315 A1 | 8/2012 | Hochschuler et al. | |

FOREIGN PATENT DOCUMENTS

| | | |
|---|---|---|
| CN | 101390773 | 11/2010 |
| CN | 101953713 | 1/2011 |
| WO | WO 2007/145937 | 12/2007 |
| WO | WO 2008/027549 | 3/2008 |
| WO | WO 2009/129063 | 10/2009 |
| WO | WO 2010/148103 | 12/2010 |
| WO | WO 2011/401398 | 4/2011 |
| WO | WO 2011/080260 | 7/2011 |
| WO | WO 2011/106711 | 9/2011 |
| WO | WO 2011/109260 | 9/2011 |

OTHER PUBLICATIONS

U.S. Appl. No. 29/476,705, Dec. 16, 2013, Frey et al.
U.S. Appl. No. 29/476,709, Dec. 16, 2013, Frey et al.
Notice of Allowance for U.S. Appl. No. 29/432,668 mailed Nov. 27, 2013, 11 pages.
Official Action for Australian Patent Application No. 2011276468 dated Apr. 10, 2013, 3 pages.
Official Action for U.S. Appl. No. 13/172,683, mailed Feb. 24, 2014, 10 pages.
Notice of Allowance for U.S. Appl. No. 13/172,683 mailed Apr. 23, 2014, 7 pages.
U.S. Appl. No. 29/432,668, filed Sep. 18, 2012, Frey.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).

(56) References Cited

OTHER PUBLICATIONS

Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).

International Search Report and Written Opinion for International (PCT) Patent Application No. PCT/US11/42412 mailed Nov. 8, 2011, 8 pages.

International Preliminary Report on Patentability for International (PCT) Patent Application No. PCT/US11/42412 mailed Jan. 17, 2013, 7 pages.

International Search Report and Written Opinion for International (PCT) Patent Application No. PCT/US2013/036535, mailed Jun. 26, 2013 8 pages.

Official Action for U.S. Appl. No. 13/172,683, mailed Sep. 10, 2013 7 pages.

Notice of Allowance for U.S. Appl. No. 29/409,734, mailed May 11, 2012 8 pages.

Notice of Allowance for U.S. Appl. No. 29/427,918, mailed Oct. 15, 2012 9 pages.

\* cited by examiner

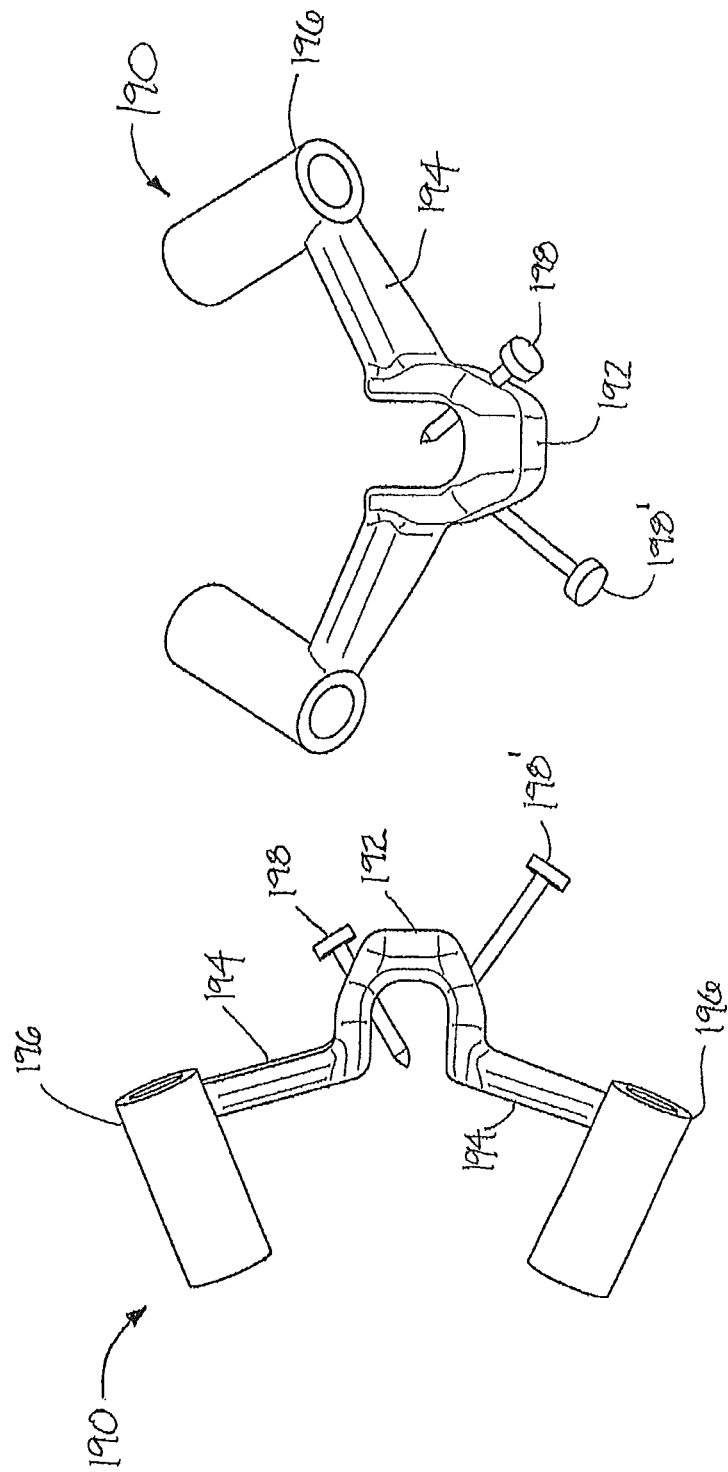

Insert Diameter for 4.5 mm Tap

Insert Diameter for 1/8" Drill Bit

FIG. 33A
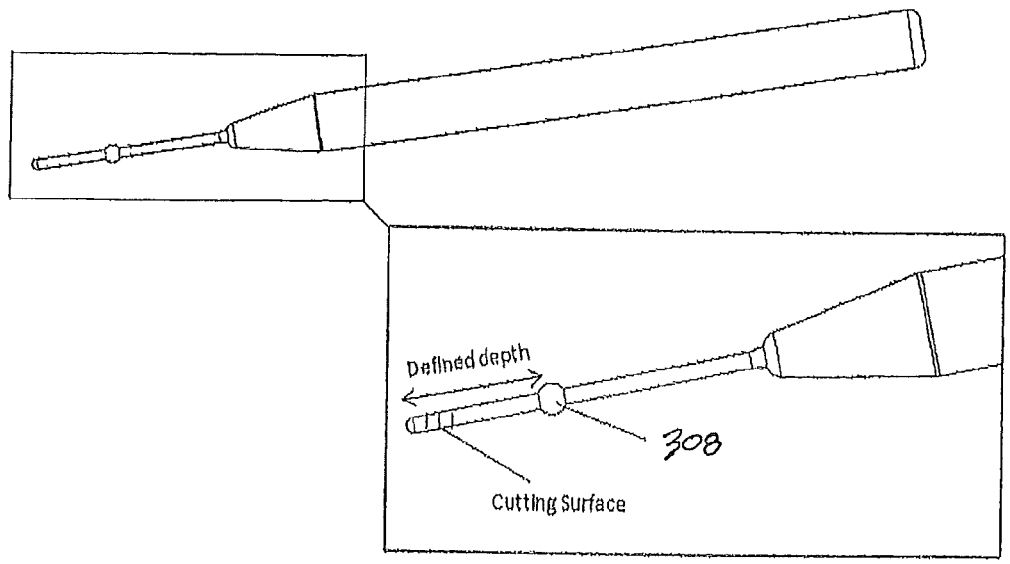
FIG. 33B
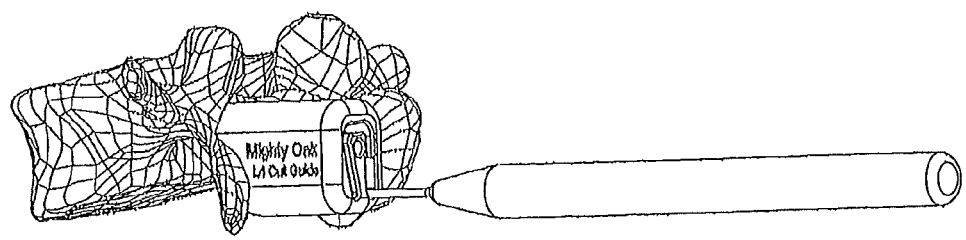
FIG. 33C

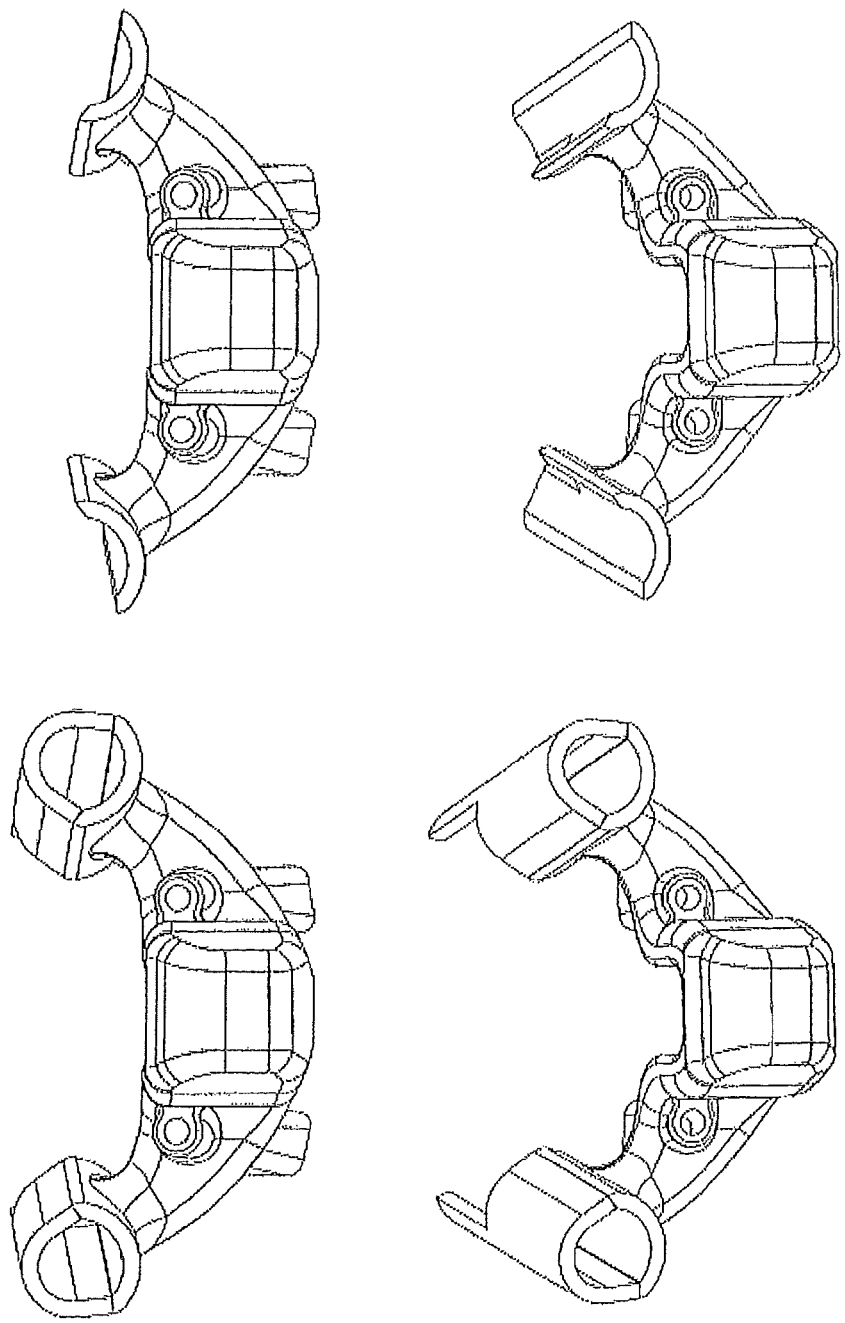
FIGURE 40 A-D

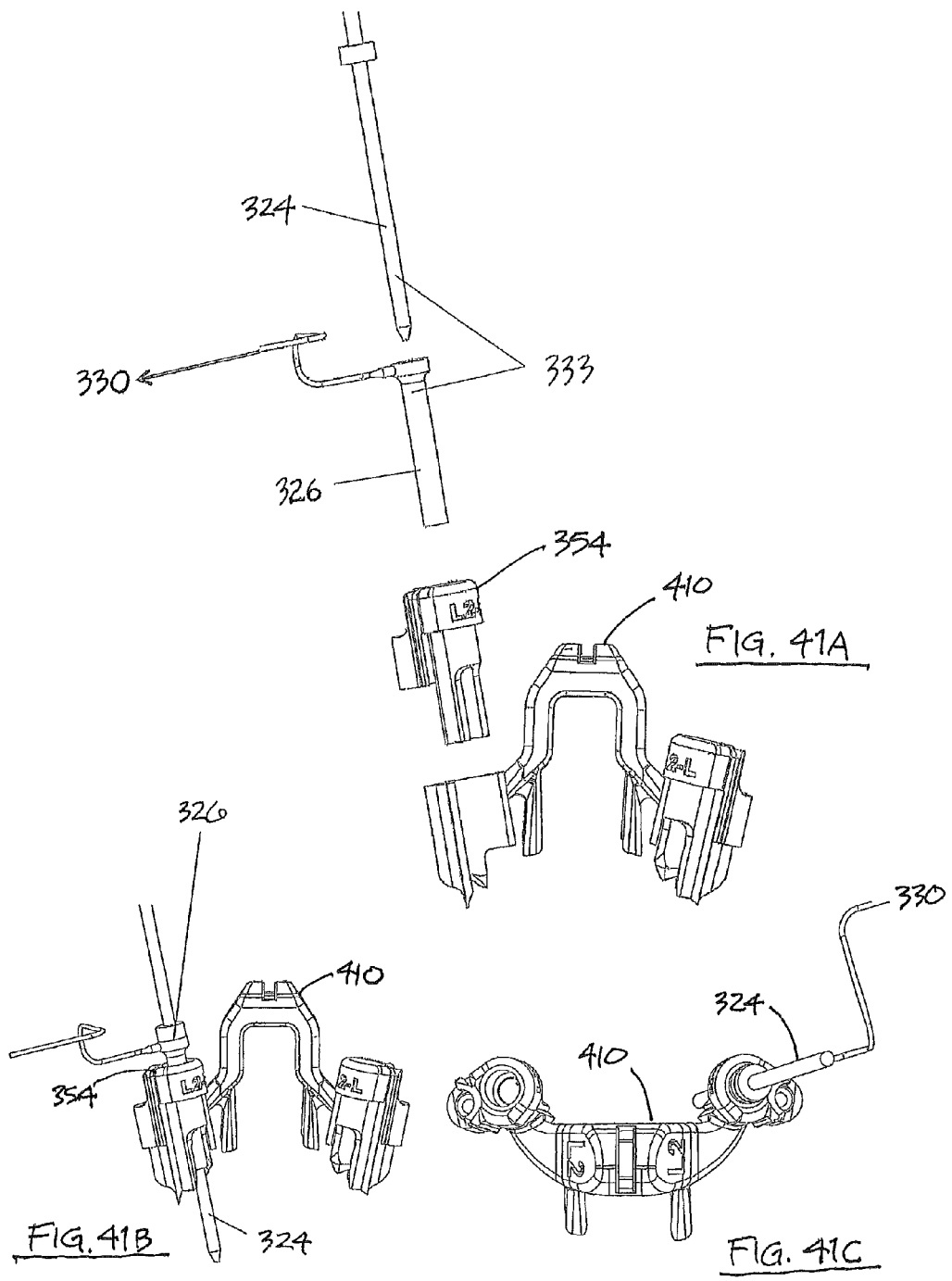

PATIENT MATCHING SURGICAL GUIDE AND METHOD FOR USING THE SAME

CROSS-REFERENCE TO RELATED APPLICATIONS

This application is a continuation-in-part of U.S. patent application Ser. No. 13/172,683, filed Jun. 29, 2011, which in turn claims priority to U.S. Provisional Patent Application Nos. 61/359,710, filed Jun. 29, 2010, and 61/393,695, filed Oct. 15, 2010. This application also claims priority to U.S. Provisional Patent Application No. 61/625,559, filed Apr. 17, 2012. These applications are all incorporated by reference herein in their entireties.

FIELD OF THE INVENTION

The present disclosure relates to the field of medical devices and is generally directed toward apparatus configurable for use with a specific patient in a surgical setting based on the patient's unique anatomical features, and methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of pedicle screws in a vertebral body (as a adjunct or stand-alone stabilization mechanism) is well accepted amongst surgeons who treat various spine pathologies, and although the performance of various pedicle screw constructs have become predictable, there are still multiple challenges with the placement and insertion of the pedicle screws or other bone anchors. The challenges occur when a surgeon is unable to reference boney landmarks due to previous surgery or when the patient's anatomy is irregular in shape.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a custom implant based on the dynamic nature of the anatomical structures the custom implant is designed to associate with. This data, while currently used by surgeons in surgery planning, is largely unused for creating a customized set of instruments or other surgical devices that are designed to complement the patient's unique anatomy.

The prior art, however, fails to teach a system for creating a suite of surgical apparatus based on the data set derived from the MRI or CT scan. For example, the use of the patient specific data set for a vertebral body may allow a surgeon to accommodate for subtle variations in the position and orientation of a plate or other bone anchor to avoid particular boney anatomy or irregularities in the positioning and alignment of the adjoining vertebral bodies. As another example, the use of these data sets may also assist a surgeon in selecting a desired trajectory for an implantable device so as to avoid, for example, crossing the pedicle wall and violating the spinal canal during an actual procedure. The use of the data sets permit the surgeon to avoid these types of mistakes by creating customized tools and instruments, which may comprise end-stops or other safety related features to avoid over-torque and over-insertion of any implantable devices. The data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures. The system and method according to this embodiment uses a patient's unique morphology, which may be derived from capturing MRI data or CT or other data to derive one or more "Patient Matched" apparatus, which comprises complementary surfaces based on a plurality of data points from the MRI or CT data. Each "Patient Matched" apparatus is matched and oriented around the patient's own anatomy, the desired insertional trajectories (which may be verified in a pre-operative setting using 3D CAD software, such as the software disclosed in WO 2008027549, which is incorporated by reference herein in its entirety), and according to one embodiment described herein, other apparatus used during the surgical procedure.

The customized and integrated matching aspects of this presently disclosed system provides an advantage over the prior art, in particular by providing a plurality of interlocking and/or matching points for each apparatus, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises the following steps:

obtaining data associated with a patient's anatomy;
converting the data obtained to a 3-dimensional data set(s);
determining at least one trajectory or path for facilitating a surgical procedure to be performed on the patient;
determining at least one surface associated with the patient's anatomy; generating a 3-dimensional representation of the customized surgical device or instrument, which incorporates the at least one trajectory of path and a matching surface to the at least one surface associated with the patient's anatomy; and
fabricating the customized surgical device or instrument using the 3-dimensional representation.

According to another aspect of the present disclosure, a system and method for facilitating a surgical procedure(s) comprises the following steps:

Obtaining data associated with the patient's anatomy by way of a MRI or CT scan;
Converting the MRI or CT scan data to a 3-Dimensional data set(s)

Determining one or more axes or planes of orientation of a device to be constructed for use in facilitating the surgical procedure(s) to be performed on the patient;

Modeling the device for use in facilitating the surgical procedure(s) using the determined axes and accounting for any other constraints derived from the converted data set(s);

Generating a prototype of the modeled device by, for example, use of rapid prototyping machinery; and Preparing the prototype for use during the surgical procedure(s).

According to this aspect described above, the method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from a radiographic imaging machine, a fluoroscopy, an ultrasonic machine or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc.

According to yet another aspect of the present disclosure, a preconfigured surgical template is disclosed, which comprises one or more guides for receiving at least one tool. According to this embodiment, the one or more guides further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed, comprising the steps of:

collecting data from the patient corresponding to the patient's unique anatomy;

creating a model of the template from the data collected, the model comprising a plurality of matching surfaces to the patient's unique anatomy;

providing data associated with model to fabrication machinery;

rapidly generating the template to comprise the plurality of matching surfaces and further comprising at least one additional matching surface corresponding to at least one tool or instrument used in the surgical operation; and generating a permanent device based on the template for use in the surgical operation.

In one embodiment of the present disclosure the model is a digital model. In another embodiment of the present disclosure the model is a physical model.

According to yet another aspect of the present disclosure, a system for performing a surgical procedure on a patient is disclosed, comprising:

a surgical guide;

the surgical guide comprising a plurality of surfaces determined from data scanned from the patient, the plurality of surfaces configured to match the patient's boney anatomy;

the surgical guide further comprising at least one trajectory or path determined from the patient's boney anatomy for facilitating the surgical procedure;

the surgical guide further comprising at least one sleeve, the sleeve comprised of a conductive material and having a first end and a second end;

an instrument comprising at least a first portion comprised of a conductive material and adapted to be received within the at least one sleeve by inserting the at least a first portion in the first end of the at least one sleeve and contact the conductive material of the at least one sleeve;

wherein the at least a first portion of the instrument is adapted to pass through the at least one sleeve and exit the second end of the at least one sleeve; and wherein the surgical guide may be subject to an electrical current for providing intraoperative monitoring (IOM) of the instrument during contact with the surgical guide and with the patient anatomy.

Further aspects of the present disclosure are directed to the system described above and further comprising a surgical guide which is subject to an electrical current by providing at least one electrode on the conductive material of the surgical guide and providing electrical current to the at least one electrode.

Further aspects of the present disclosure provide a method for manufacturing a surgical guide at an off-site manufacturing location, an on-site manufacturing location, a clinic, a surgery center, a surgeon's offices, a public hospital or at a private hospital.

Still further aspects of the present disclosure include a surgical guide manufactured using one of the methods described herein, wherein the guide is manufactured by a process selected from the group consisting of a rapid prototyping machine, a stereolithography (SLA) machine, a selective laser sintering (SLS) machine, a selective heat sintering (SHM) machine, a fused deposition modeling (FDM) machine, a direct metal laser sintering (DMLS) machine, a powder bed printing (PP) machine, a digital light processing (DLP) machine, an inkjet photo resin machine, and an electron beam melting (EBM) machine.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356 and 7,658,610, and U.S. Pat. Pub. Nos. 2010/0217336, 2009/0138020, 2009/0087276 and 2008/0114370.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a perspective view of a three-dimensional model of a unique grouping of anatomical features from which a set of data points may be derived according to one embodiment of the present disclosure;

FIG. 2 is a flow chart diagram showing the various steps of performing a method of manufacturing and using an apparatus for facilitating a surgical procedure according to one embodiment of the present disclosure;

FIG. 3 is a side elevation view of a particular apparatus for facilitating a surgical procedure according to one embodiment of the present disclosure;

FIG. 4 is rear elevation view of the apparatus shown in FIG. 3;

FIG. 5 is a top plan view of the apparatus shown in FIG. 3, relative to a unique grouping of anatomical features, and according to one embodiment of the present disclosure;

FIG. 6 is a perspective view of the apparatus and unique grouping of anatomical features shown in FIG. 5;

FIG. 7 is another perspective view of the apparatus shown in FIG. 3 demonstrating the customized patient-matching surfaces of the apparatus;

FIG. 8 is a perspective view of an apparatus according to an alternative embodiment of the present disclosure;

FIG. 9 is a perspective view of an apparatus according to yet another alternative embodiment of the present disclosure.

FIG. 10 is another perspective view of the apparatus shown in FIG. 3 along with a custom fabricated instrument for use during a particular surgical procedure;

Figure 11A:
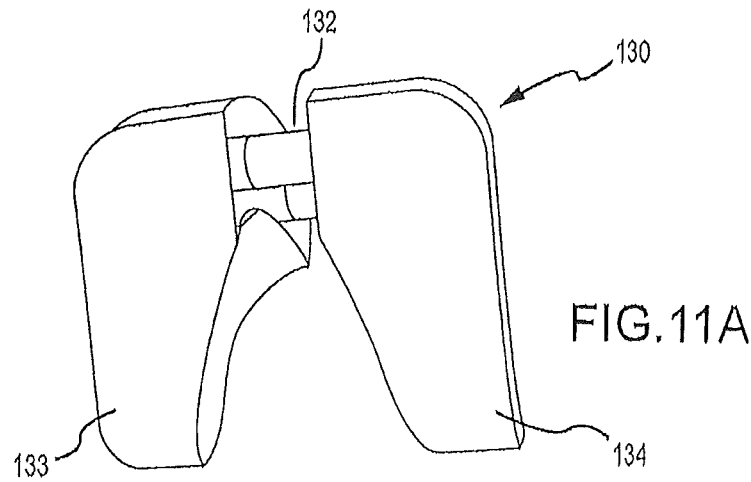
Figure 11B:
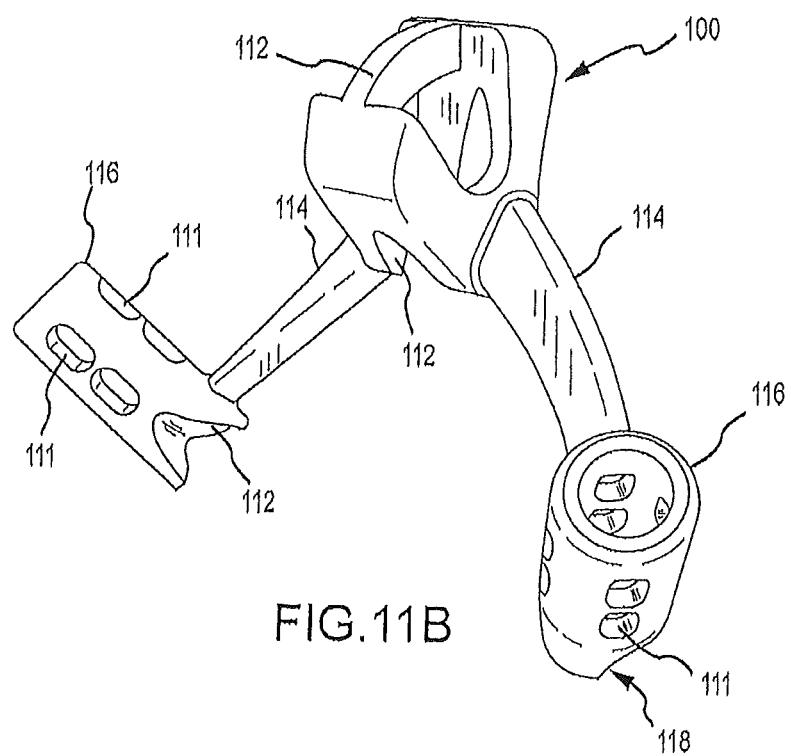
Figure 12:
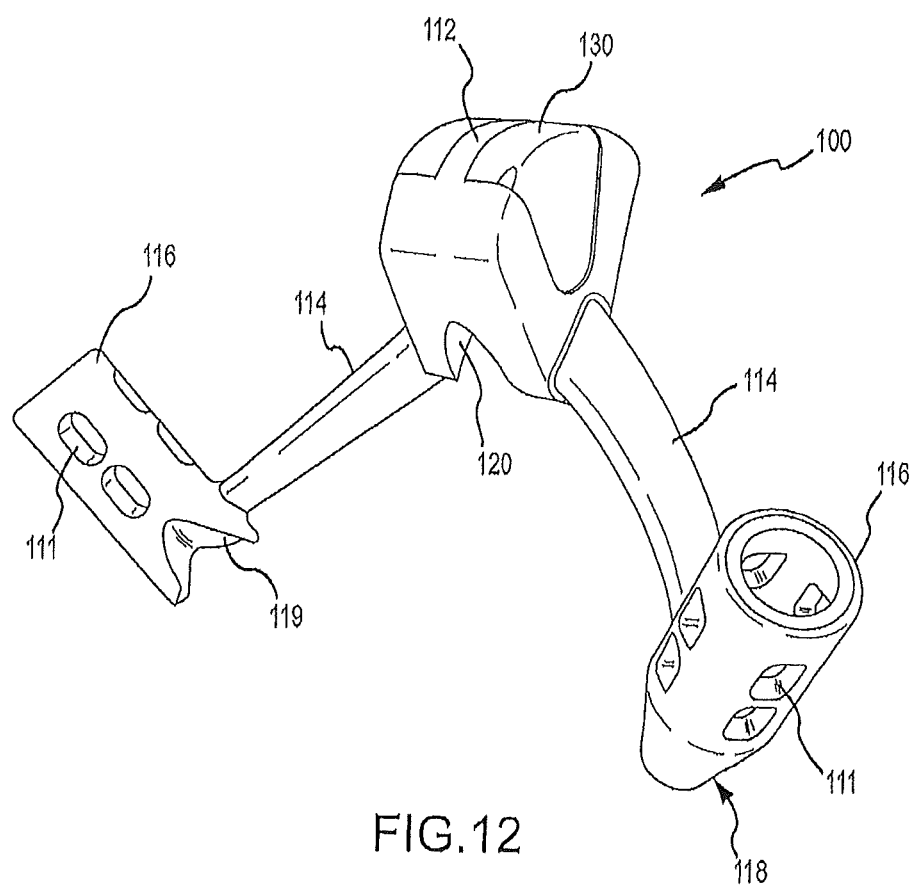
Figure 13:
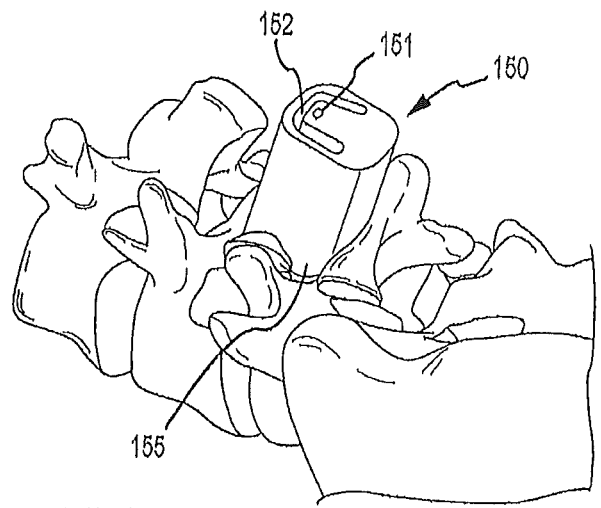
Figure 14:
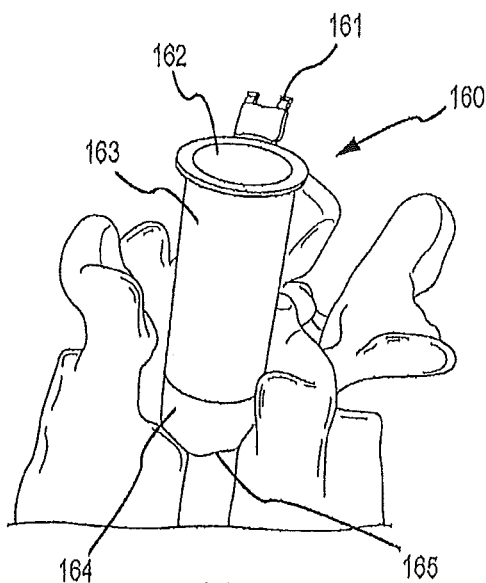
Figure 15:
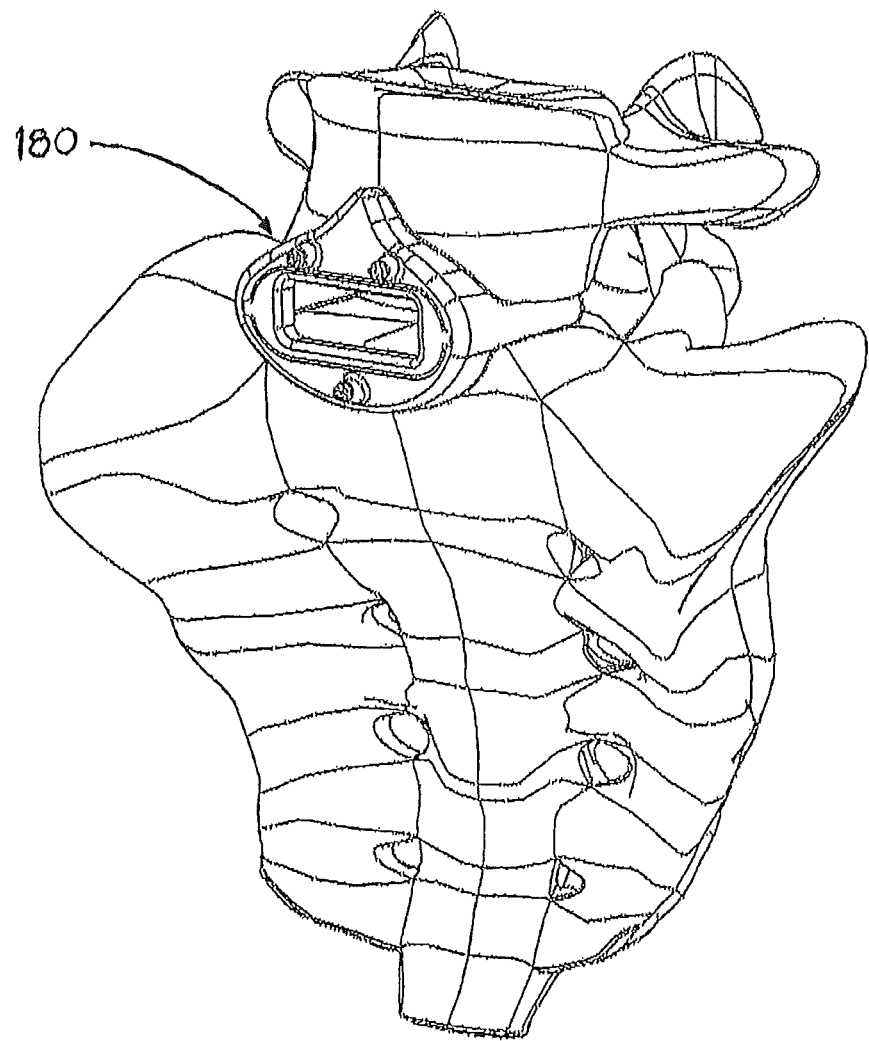
Figure 16:
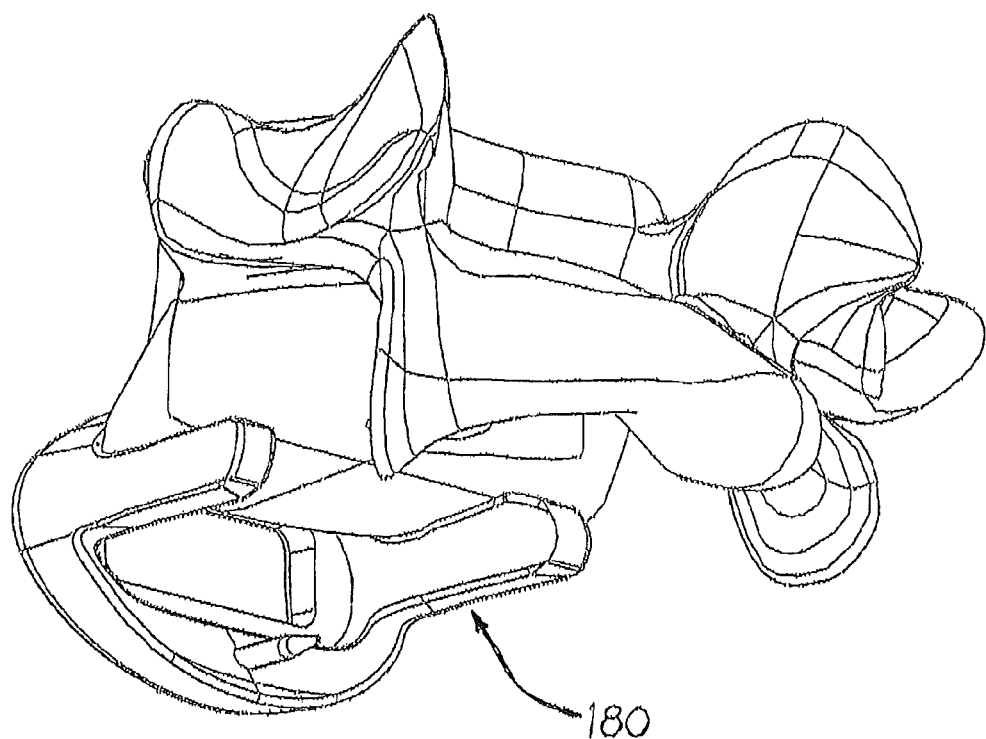
Figure 17:
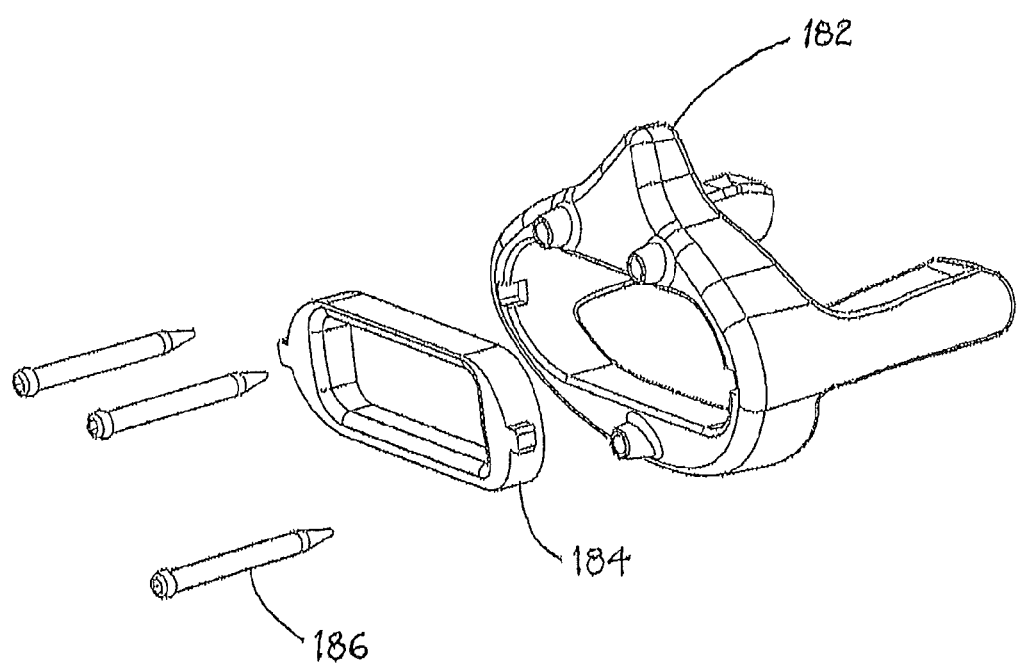

FIGS. 11A-B are perspective views of an apparatus according to another alternative embodiment of the present disclosure;

FIG. 12 is a perspective view of the apparatus shown in FIGS. 11A-B in an assembled state;

FIG. 13 is a perspective view of an apparatus according to yet another alternative embodiment of the present disclosure;

FIG. 14 is a perspective view of an apparatus according to yet another alternative embodiment of the present disclosure;

FIG. 15 is a perspective view according to yet another alternative embodiment of the present disclosure;

FIG. 16 is a different perspective view of the apparatus shown in FIG. 15;

FIG. 17 is an exploded perspective view of the apparatus shown in FIG. 15.

Figure 20:
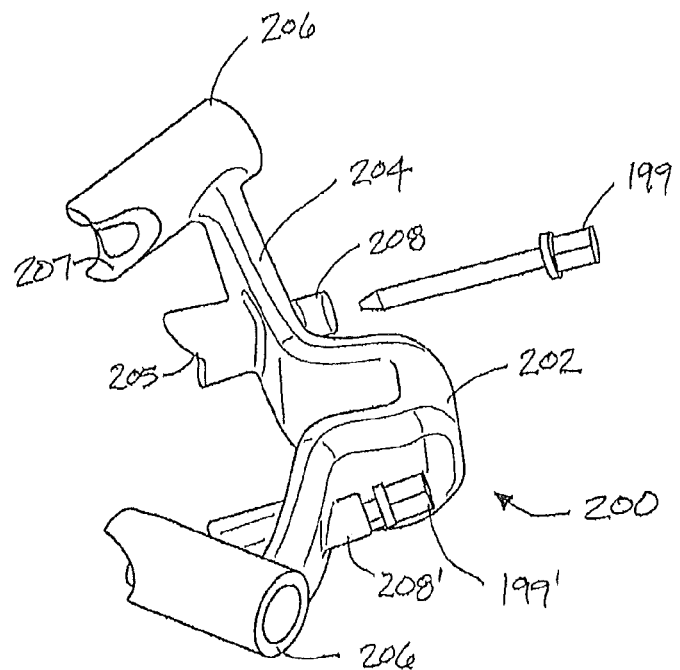
Figure 21:
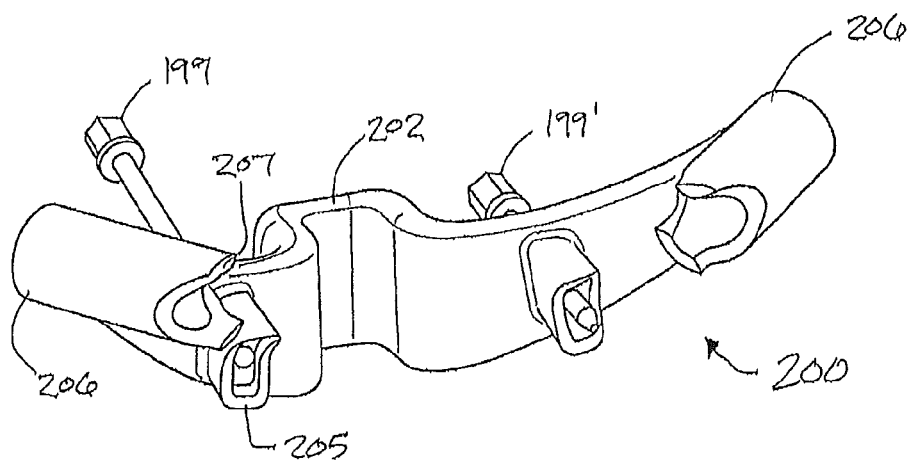
Figure 22:
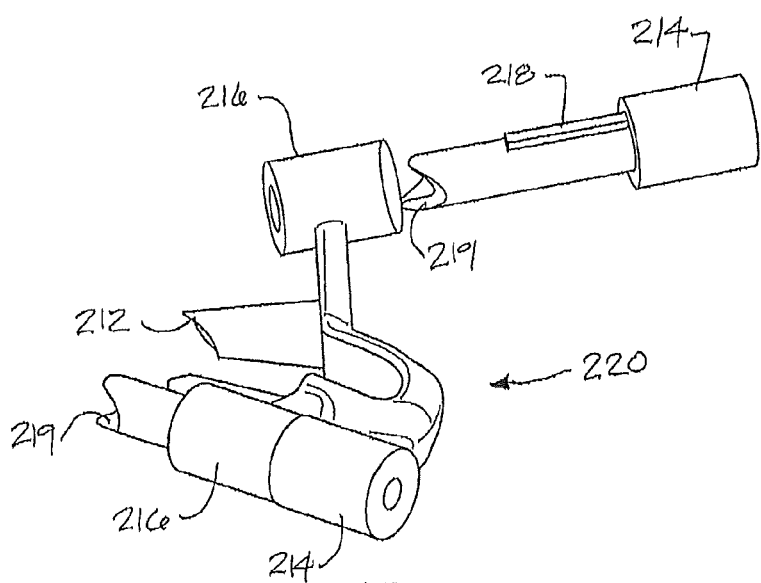
Figure 23:
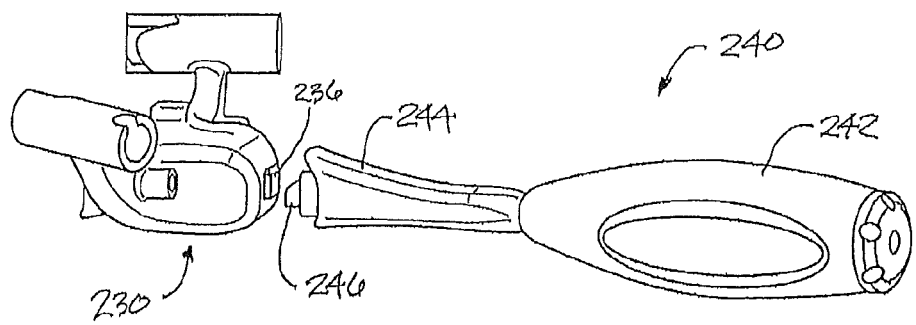
Figure 24:
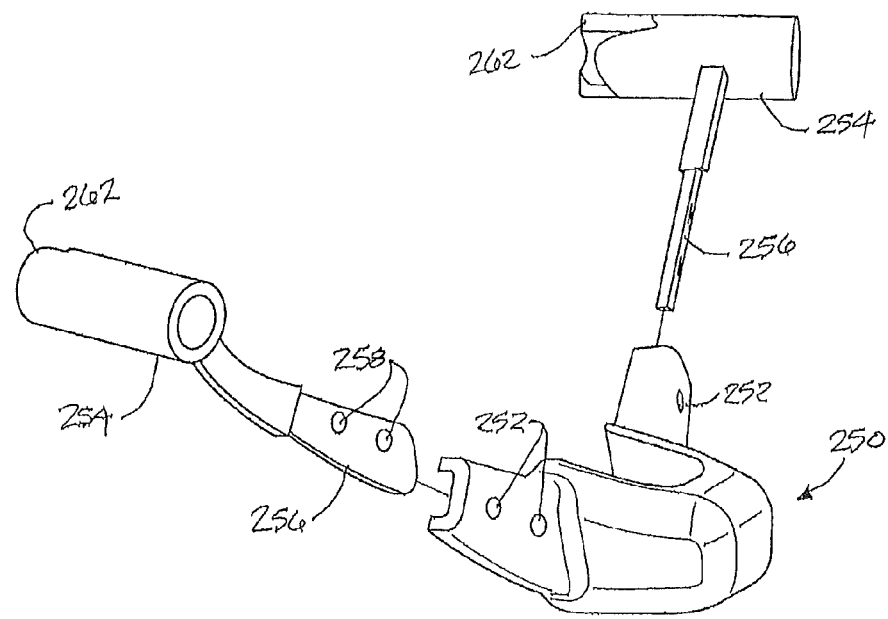
Figure 25:
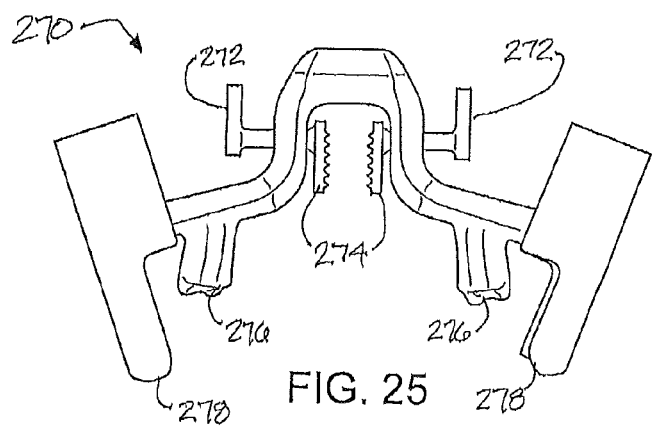
Figures 26A, 26B:
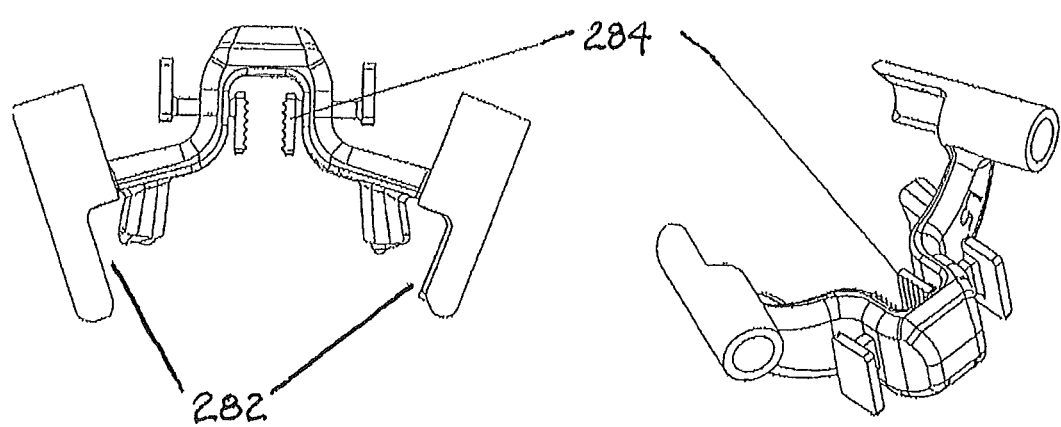
Figures 27A, 27B:
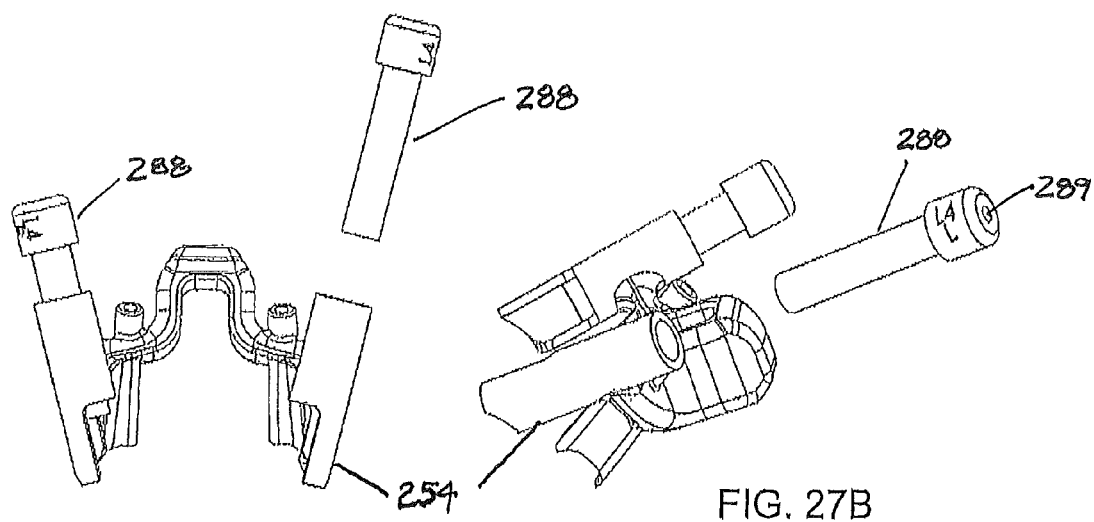
Figure 28:
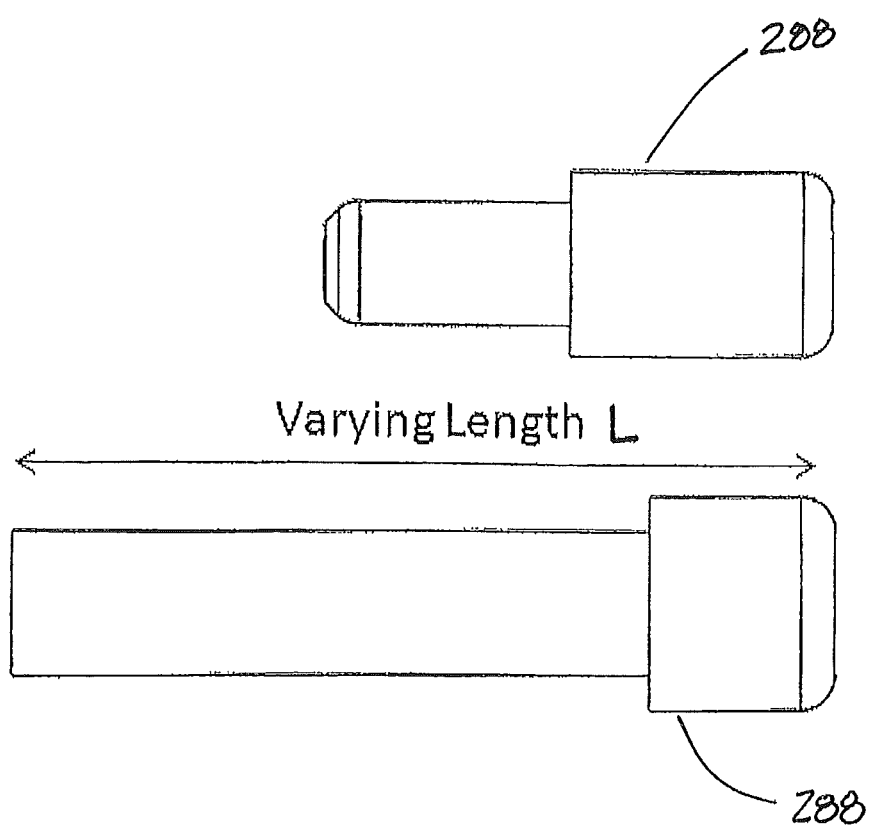
Figure 29A:
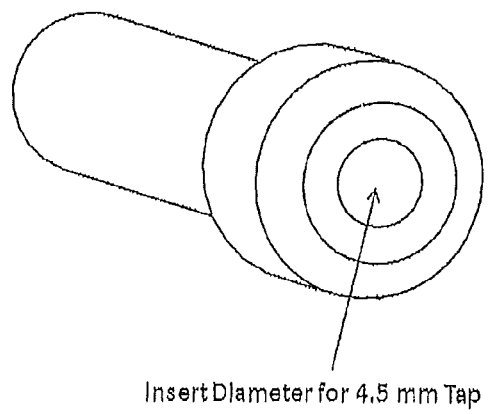
Figure 29B:
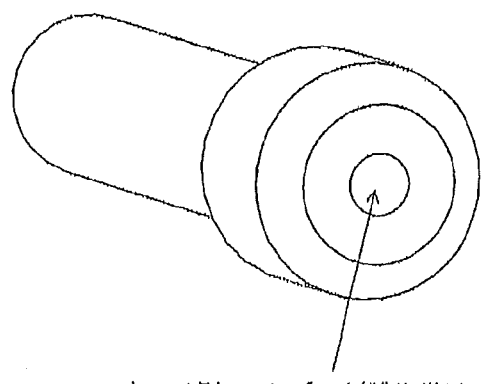
Figure 30:
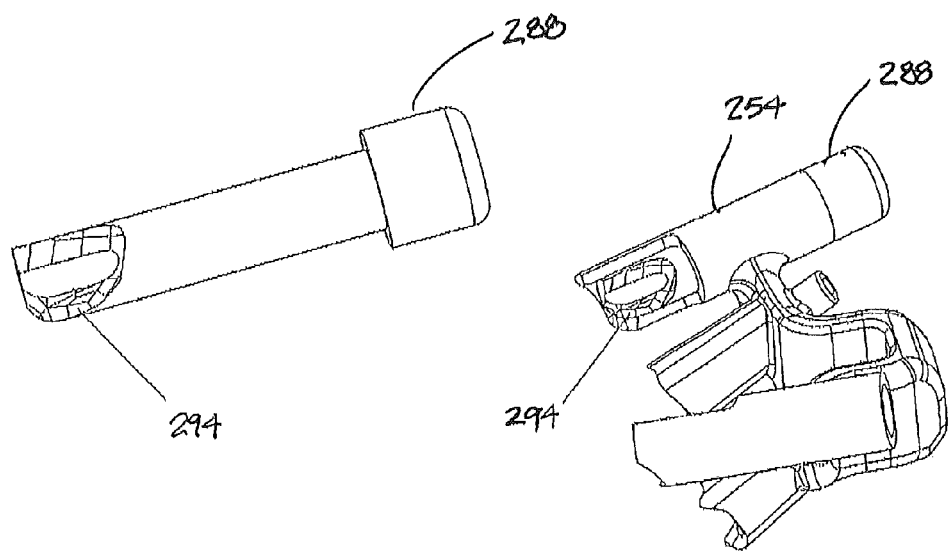
Figure 31:
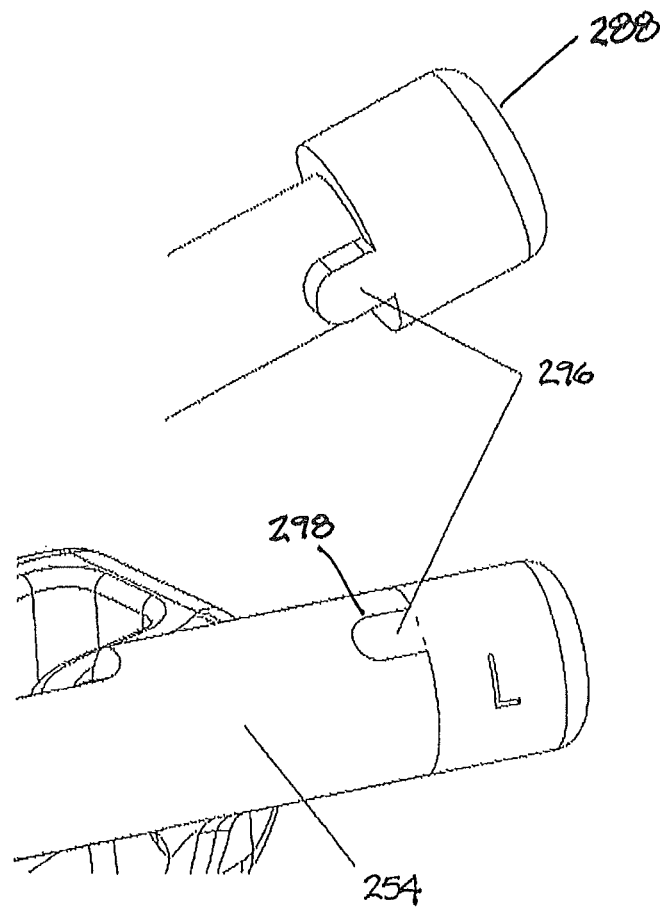
Figure 32A:
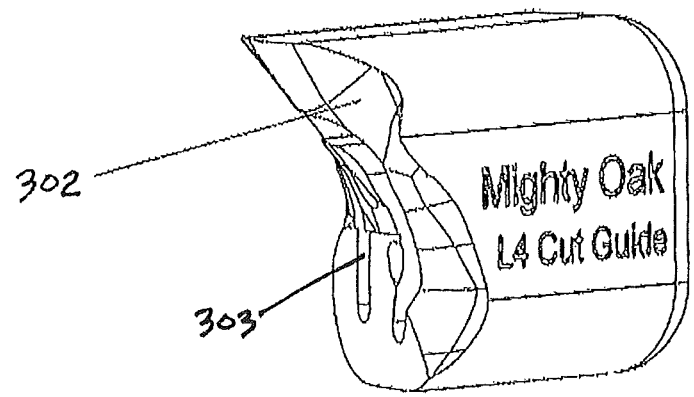
Figure 32B:
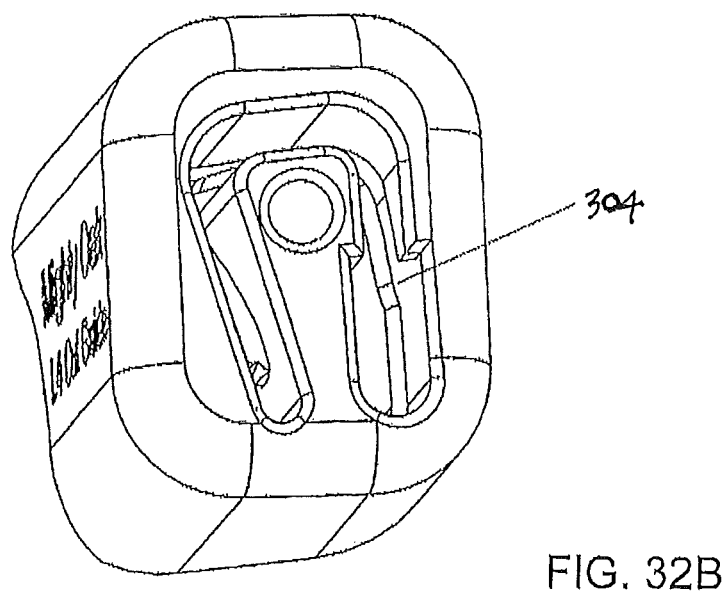
Figure 34A:
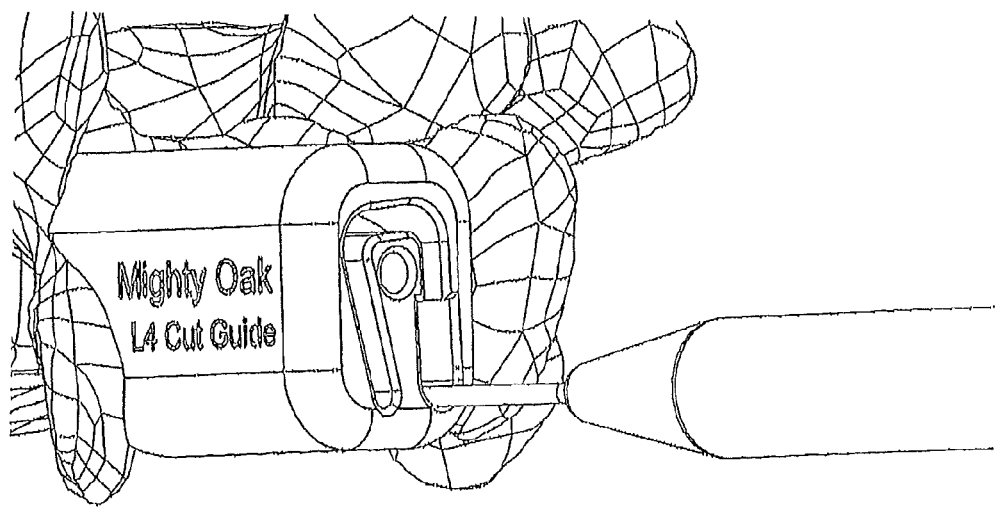
Figure 34B:
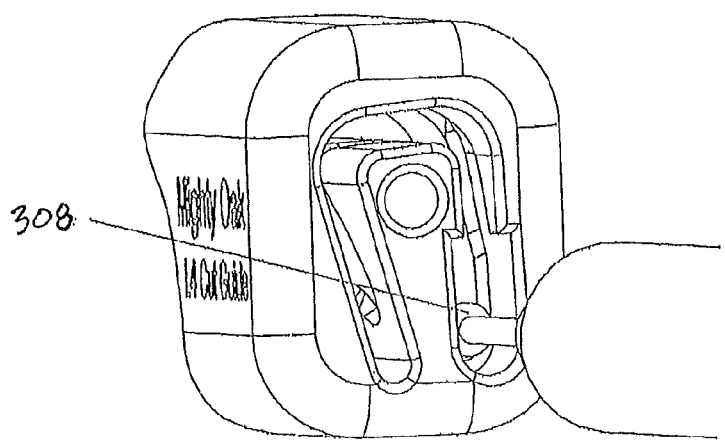
Figure 35:
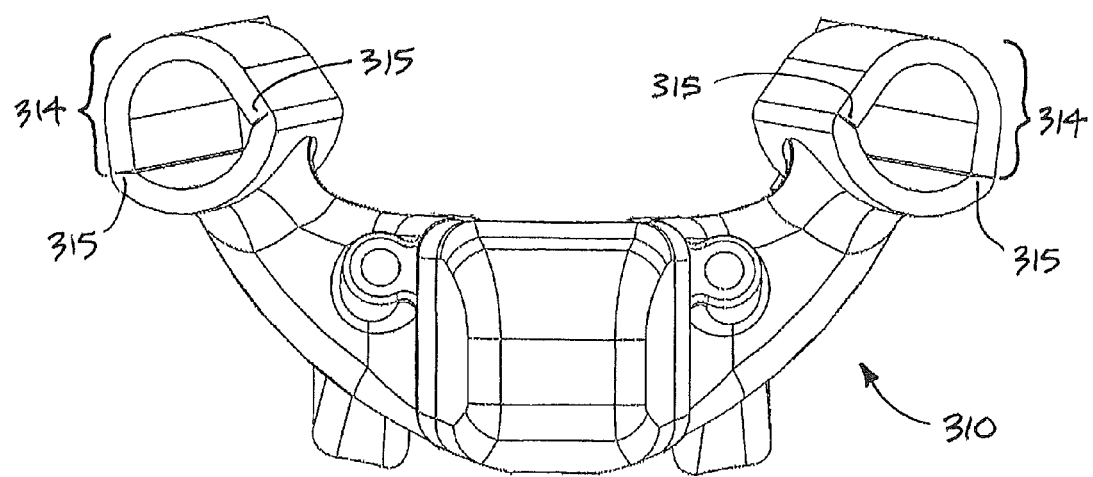
Figure 36:
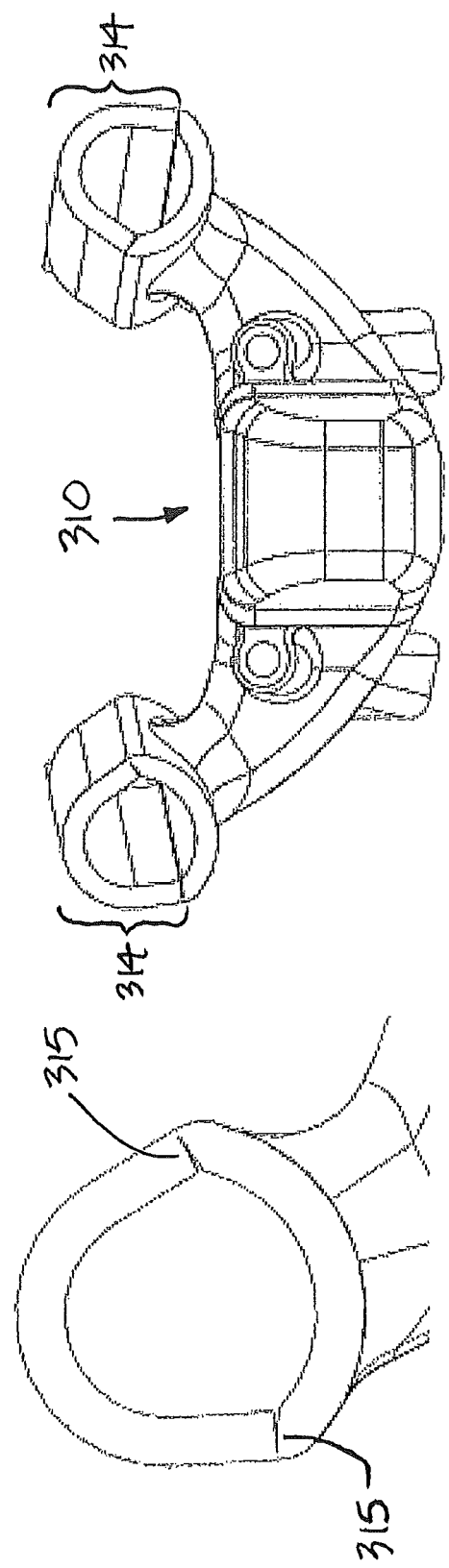
Figure 37:
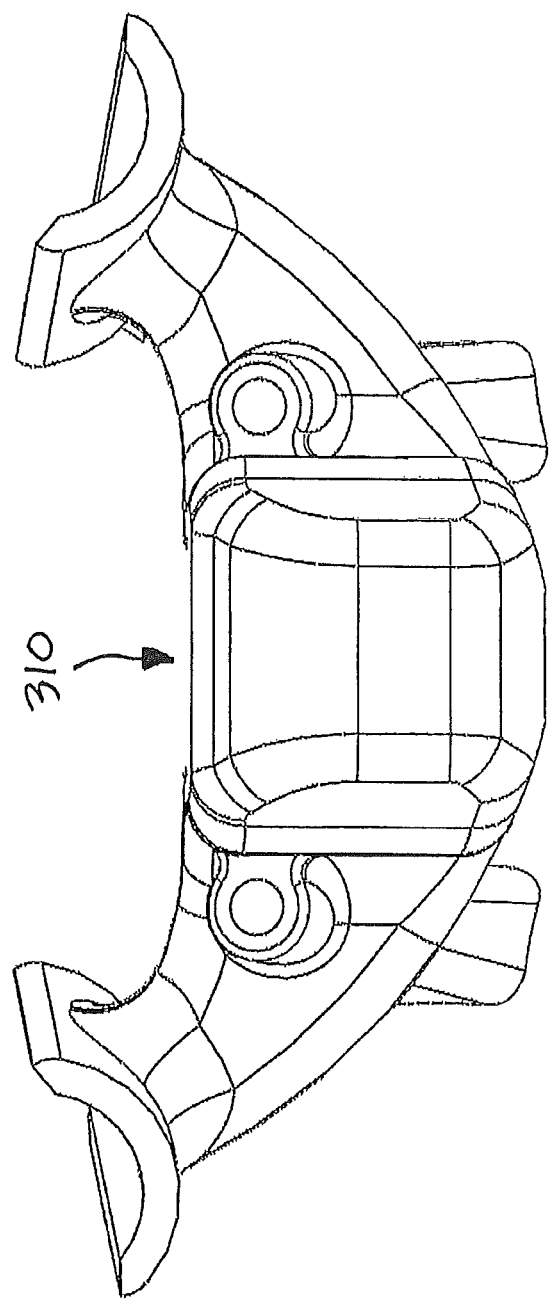
Figure 38:
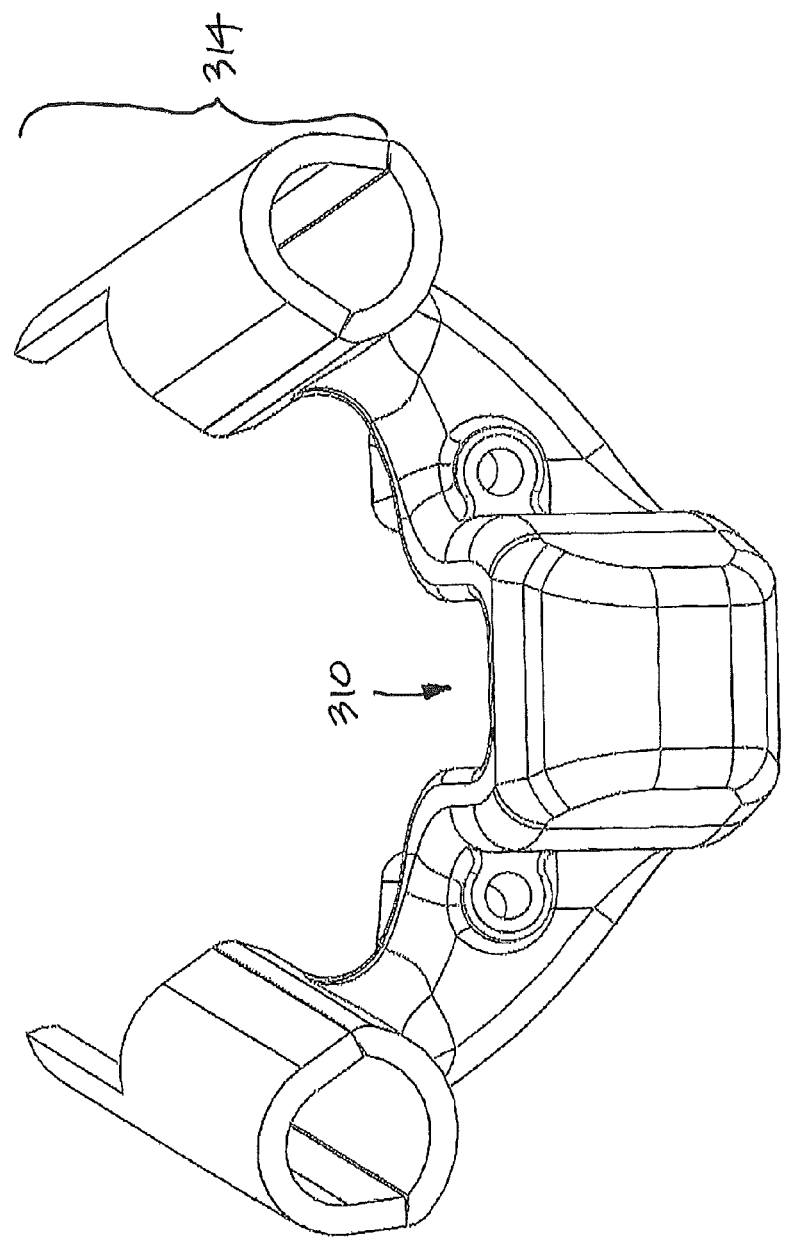
Figure 39:
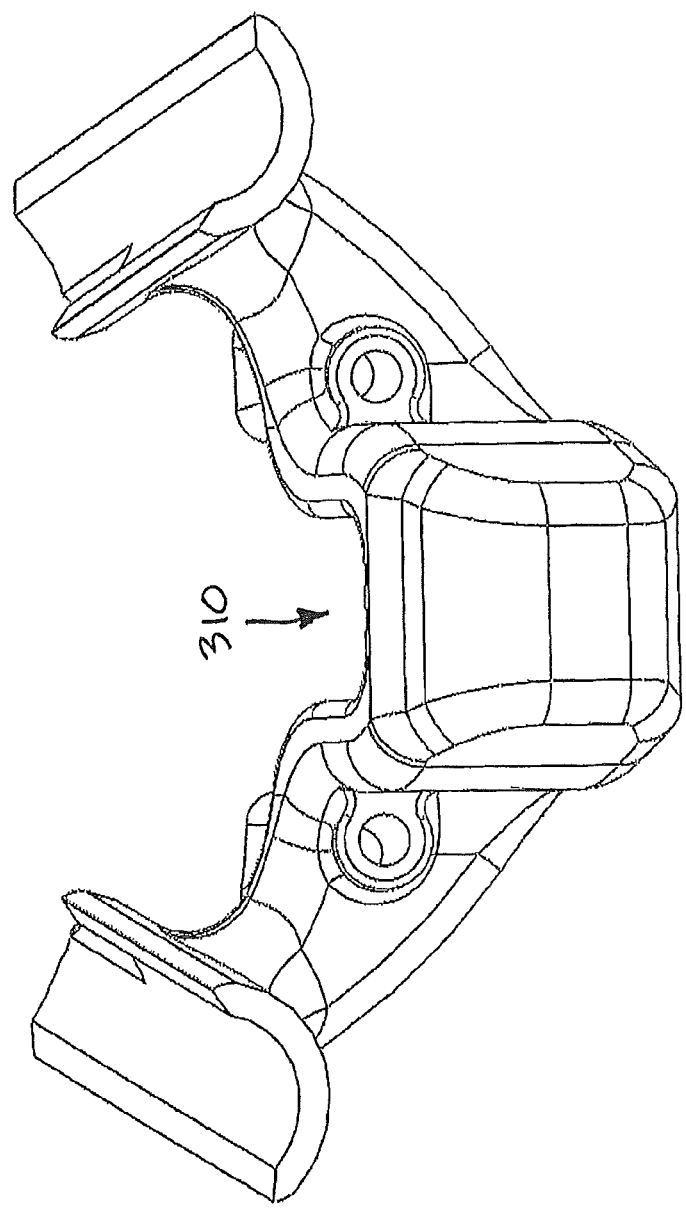
Figure 42A:
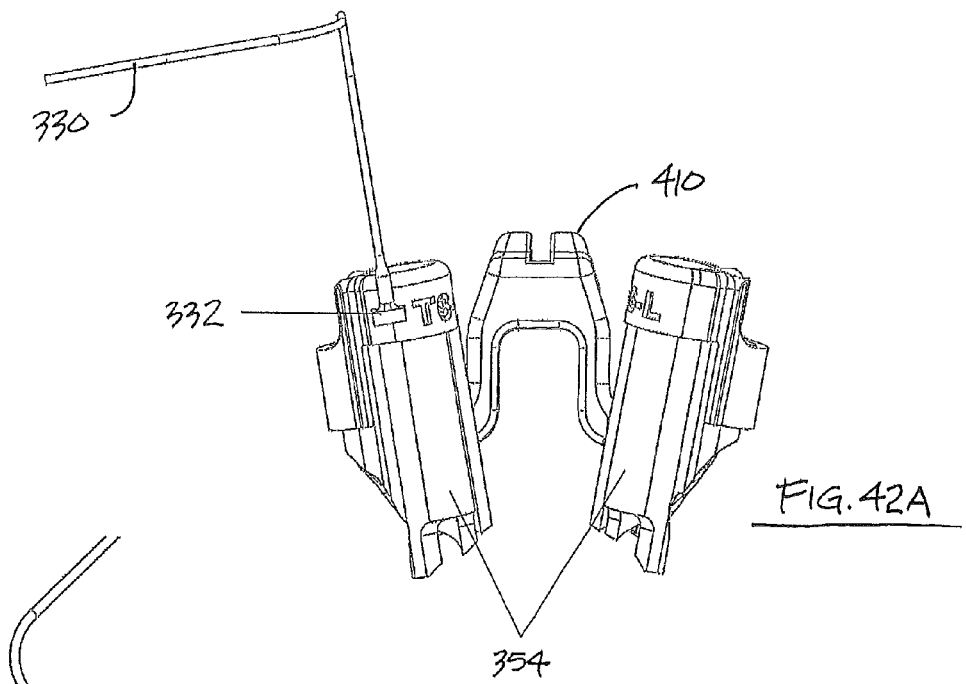
Figure 42B:
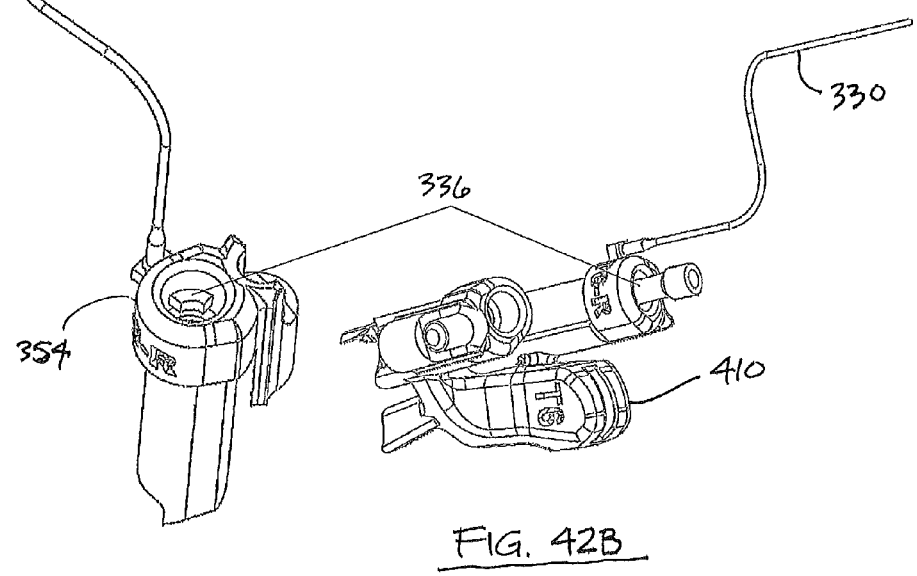
Figure 43:
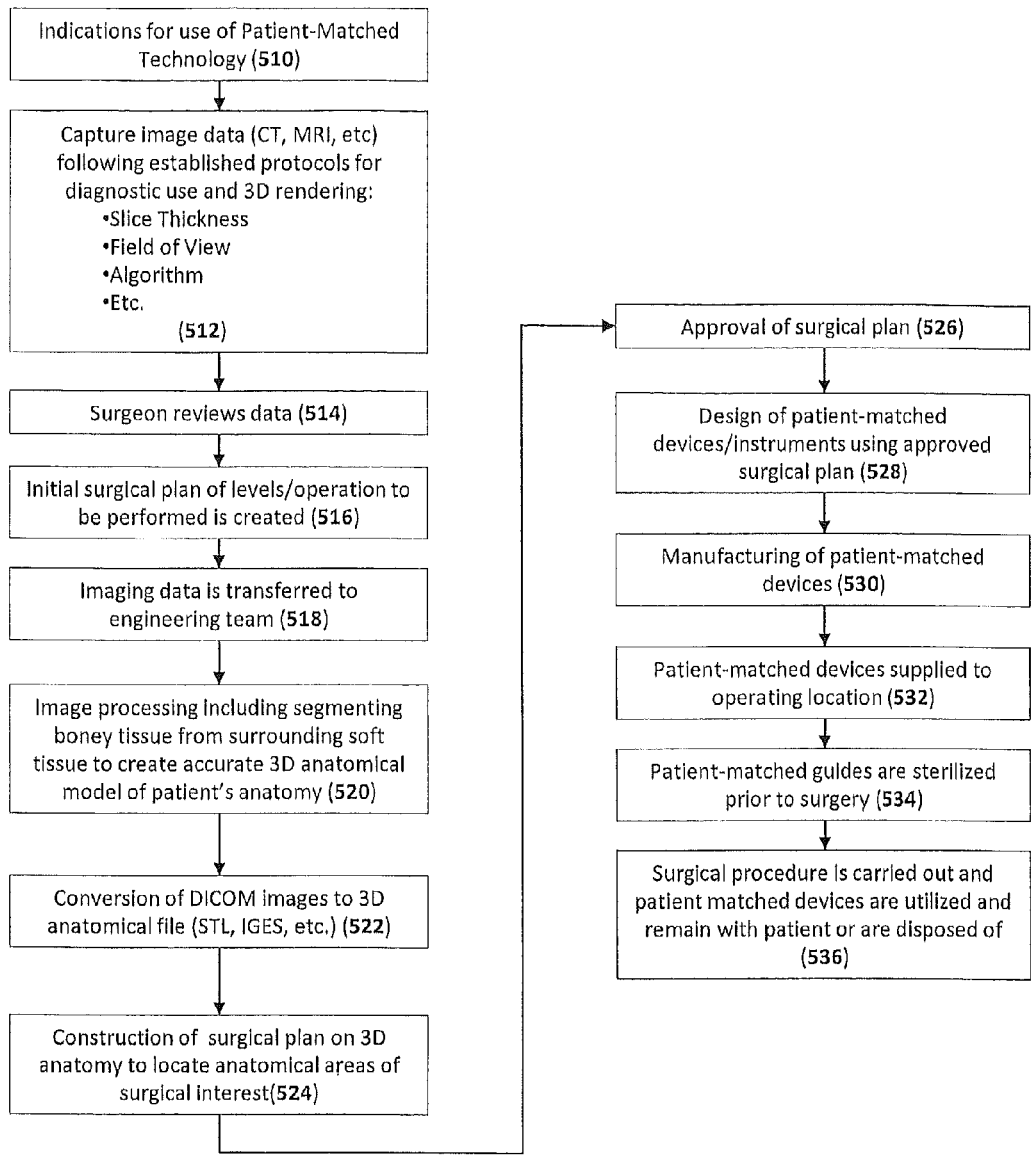

FIGS. 18-19 are perspective views according to yet another alternative embodiment of the present disclosure;

FIGS. 20-21 are perspective views according to yet another alternative embodiment of the present disclosure;

FIG. 22 is a perspective view according to yet another alternative embodiment of the present disclosure;

FIG. 23 is a perspective view according to yet another alternative embodiment of the present disclosure;

FIG. 24 is a perspective view according to yet another alternative embodiment of the present disclosure;

FIG. 25 is a perspective view according to yet another alternative embodiment of the present disclosure;

FIG. 26A is a perspective view according to yet another alternative embodiment of the present disclosure;

FIG. 26B is a perspective view according to the embodiment shown in FIG. 26A;

FIG. 27A is a front elevation view according to yet another alternative embodiment of the present disclosure;

FIG. 27B is a perspective view according to the embodiment shown in FIG. 27A;

FIG. 28 is an elevation view according to yet another alternative embodiment of the present disclosure;

FIG. 29A is a perspective view according to yet another alternative embodiment of the present disclosure;

FIG. 29B is a perspective view according to yet another alternative embodiment of the present disclosure;

FIG. 30 is a perspective view according to yet another alternative embodiment of the present disclosure;

FIG. 31 is a perspective view according to yet another alternative embodiment of the present disclosure;

FIG. 32A is a perspective view according to yet another alternative embodiment of the present disclosure;

FIG. 32B is a perspective view according to the embodiment shown in FIG. 32A;

FIG. 33A is a perspective view according to yet another alternative embodiment of the present disclosure;

FIG. 33B is a perspective view according to the embodiment shown in FIG. 33A;

FIG. 33C is another perspective view according to the embodiment shown in FIG. 33A depicted with the cutting guide of FIG. 32A;

FIG. 34A is a perspective view according to yet another alternative embodiment of the present disclosure;

FIG. 34B is a perspective view according to yet another alternative embodiment of the present disclosure;

FIG. 35 is a top plan view according to yet another alternative embodiment of the present disclosure;

FIG. 36 is a detailed view of the device according to the embodiment shown in FIG. 35;

FIG. 37 is another top plan view of the device according to the embodiment shown in FIG. 35;

FIG. 38 is a top plan view according to yet another alternative embodiment of the present disclosure;

FIG. 39 is another top plan view of the device according to the embodiment shown in FIG. 38;

FIGS. 40A-D are additional top plan views of the devices according to the embodiments shown in FIGS. 35-39;

FIGS. 41A-C are perspective views of devices and instruments according to one alternative embodiment of the present disclosure, which includes an EMG sensor and the ability to transmit EMG data to a monitoring apparatus;

FIGS. 42A-B include additional perspective views of the embodiment shown in FIGS. 41A-C; and FIG. 43 is a diagram of the steps of a method for fabricating a device or instrument according to an alternate embodiment of the present disclosure.

DETAILED DESCRIPTION

As shown in the appended Figures and described in further detail herein, the present disclosure relates to a novel system and method for developing a variety of customized, patient-matched apparatus for use in a diverse number of surgical procedures. The system and method uses a patient's unique morphology, which may be derived from capturing MRI data or CT data to derive one or more patient-matched apparatus, which comprise complementary surfaces to those encountered during the surgical procedure(s) as derived from a set of data points. According to various embodiments described herein, the patient-matched apparatus may further comprise desired axes and/or insertional trajectories. According to one alternate embodiment described herein, the patient-matched apparatus may be further matched with at least other apparatus used during the surgical procedure. Other features of the disclosure will become apparent after a review of the following disclosures and varying embodiments of the invention.

Figure 1:
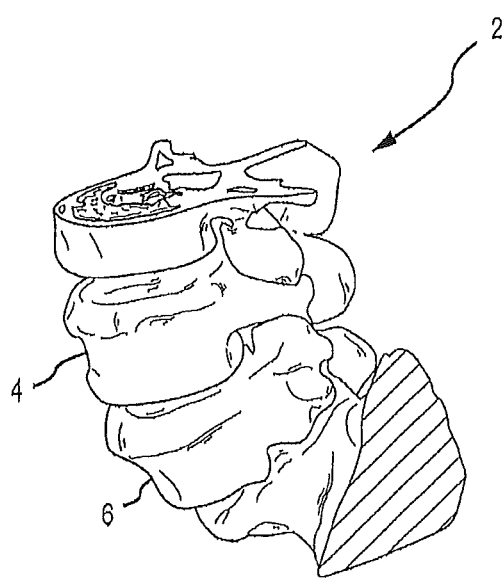

Multiple embodiments of the disclosure are depicted in FIGS. 1-43. Referring now to FIG. 1, a perspective view of a three-dimensional model of a unique grouping of anatomical features according to one embodiment of the present disclosure is shown. Here, the model 2 is comprised of multiple vertebral bodies 4, 6 but according to other embodiments may be comprised of any anatomical grouping for a particular patient. Data associated with the model 2 may be captured from a MRI or CT scan or from radiographic images of the patient's corresponding boney anatomy (or alternatively from other data sources). The data, once captured, may be converted using known software tools to a CAD program, where the data set is representative of the model 2 and may be used to provide additional data points for forming the contours, sizes, shapes and orientations of one or more apparatus to be used in the surgical procedure.

According to an alternative embodiment, the data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

Figure 2:
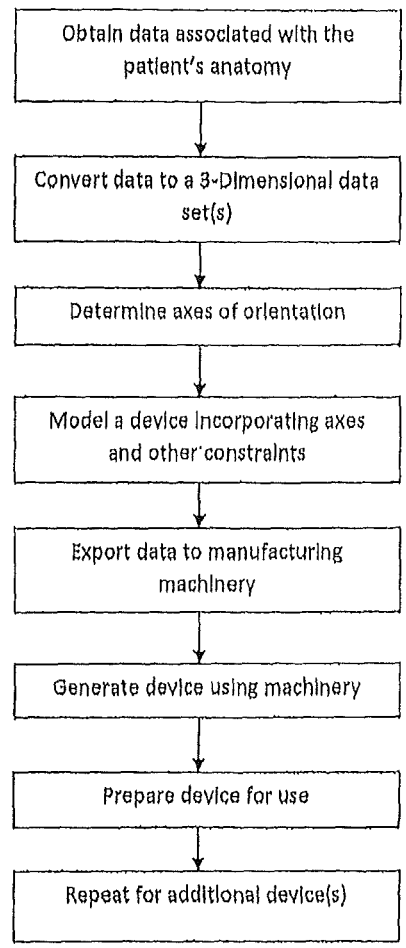

FIG. 2 is a flow chart showing the various steps of performing a method of manufacturing an apparatus, according to various embodiments described herein, for use in facilitating a surgical procedure. The method, according to a preferred embodiment, comprises the following steps:

A) Obtaining data associated with the patient's anatomy by way of a MRI or CT scan;

B) Converting the MRI or CT scan data to a 3-Dimensional data set(s)

C) Determining one or more axes of orientation of a device to be constructed for use in facilitating the surgical procedure(s) to be performed on the patient;

D) Modeling the device for use in facilitating the surgical procedure(s) using the determined axes and accounting for any other constraints derived from the converted data set(s);

E) Generating a prototype of the modeled device by, for example, use of rapid prototyping machinery; and F) Preparing the prototype for use during the surgical procedure(s).

As shown in FIG. 2, the method may comprise additional steps or may be repeated for additional devices used in the surgical procedure. The step of obtaining data is typically performed in a traditional manner, by subjecting the patient to a scan using MRI or CT or other suitable scanning equipment known in the art. The data is then captured by the equipment and may be converted to a 3-Dimensional data set(s) by software or other algorithmic means known in the art, such as by exporting the data into a known modeling software program that allows data to be represented, for example, in CAD format. Once this data is converted, a device may be modeled to complement the data set(s) and oriented by one or more axes determined by the surgeon either before or through observation of the data set(s) from the initial scan of the patient's anatomy.

The method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc. The prototype may be generated using known rapid prototyping machinery, or alternatively by milling machinery such as a CNC milling machine. Alternatively, the initial device fabricated by this method may be in a temporary state for further consideration and or manipulation by the surgeon, and then finally constructed using one of the methodologies described herein. The steps may be repeated for complementary devices, some or all of which may include further matching surfaces for the patient's anatomy or to the previously fabricated devices (i.e., the devices fabricated may have matching surfaces for adjoining together one or more devices, as described in greater detail below).

Alternatively, the system and method described herein may facilitate the alignment of various anatomical features for a particular patient, such as, for example, multiple vertebral bodies in a patient to correct spinal deformities. For example, the data set(s) may provide an initial location for the anatomical features, but may be further manipulated by the surgeon in a pre-operative setting to create a desired data set(s), such as a final location for the anatomical features once the surgical procedure(s) are completed. In this manner, the devices formed by the system and method described above may be used in either an initial location or a final location for the anatomical features, and be matched to those specific locations and orientations for each stage of the surgical procedure. These staged devices would in turn provide the surgeon with a visual guide to determine the degree of correction achieved through the surgical procedure, as compared to the pre-operative plan. Other variations on the method of the present disclosure are described in the Summary of the Invention and included in the appended claims.

Fabrication methods may comprise the use of a rapid prototyping machine, such as a stereolithography (STL) machine, selective laser sintering (SLS) machine, or a fused deposition modeling (FDM) machine, direct metal laser sintering (DMLS), electron beam melting (EBM) machine, or other additive manufacturing machine. One example of such a rapid prototyping machine is commercially available from 3D Systems and known as Model SLA-250/50. The rapid prototyping machine selectively hardens a liquid, powdered or other non-hardened resin or metal into a three-dimensional structure, which can be separated from the remaining non-hardened resin, washed/sterilized and used directly as the apparatus. The prototyping machine receives the individual digital data sets and produces one structure corresponding to each of the desired apparatus.

Generally, because stereolithographic machinery produces a resin, which may have less than optimal mechanical properties (which may not be generally acceptable for a particular surgical use), the prototyping machine may alternatively be used to produce a mold. After the model is prepared, a conventional pressure or vacuum molding machine may be used to produce the apparatus from a more suitable material, such as stainless steel, titanium alloy, aluminum alloy, chromium alloy, PEEK, carbon fiber, or other metals or metal alloys.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

According to one particular embodiment of the present disclosure, a system and method is provided for fabricating apparatus for use with a variety of surgical procedures associated with a patient's spine. Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury.

For patients with varying degrees of degenerative disc disease and/or nerve compression with associated lower back pain, spinal fusion surgery, or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, thoracic or cervical spine region of a patient. Fusion requires tools for accessing the vertebrae and implanting the desired implant, any bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments. The insertion, alignment and placement of these tools, instruments and fixation devices are critical to the success of the operation. As such, providing a customized and patient-specific tool or instrument increases the likelihood that the surgical procedure will be successful.

Figure 3:
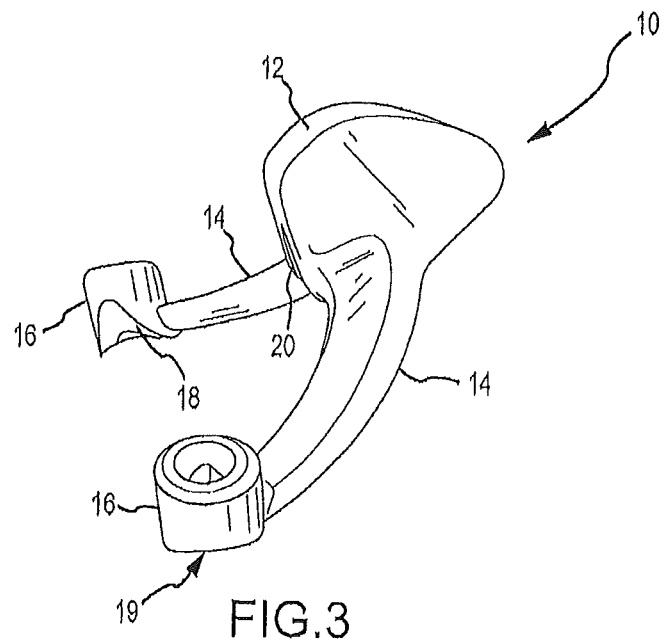
Figure 4:
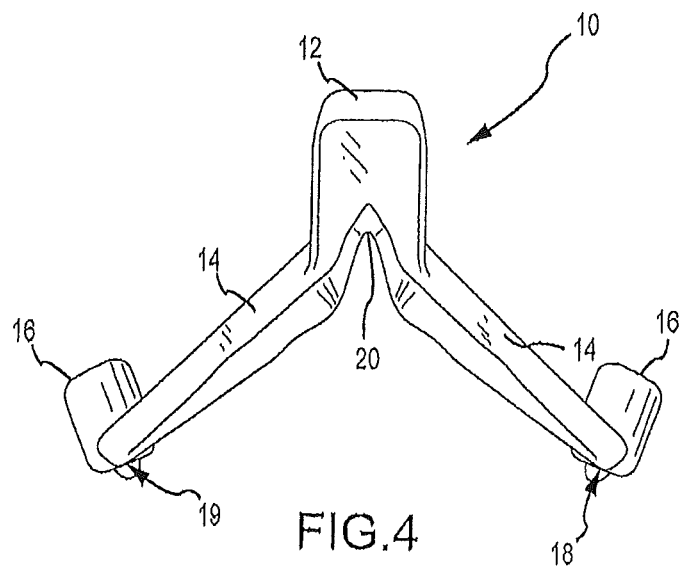

For example, one particular apparatus formed by the system and method described above and that may be used for a particular fixation related surgery is depicted in FIGS. 3 and 4. According to one embodiment of the present disclosure, the apparatus may be in the form of a pedicle screw guide 10, which is comprised of a medial body 12 and two generally elongated wings 14, each wing 14 terminating in a generally cylindrical column 16. In a preferred embodiment each of the cylindrical columns 16 is substantially hollow to permit one or more types of devices to be inserted therethrough, as depicted in FIG. 3. The medial body 12 further comprises a longitudinal cavity 20 formed about a lower surface of the medial body 12 (shown from the perspective view taken in FIG. 3). Each of the cylindrical columns 16 further comprise a lower, patient-contacting surface 18, 19, which in conjunction with the longitudinal cavity 20 provide a plurality of patient specific contours for matching with a plurality of anatomical features, as described in greater detail below.

The contours and locations of the lower, patient-contacting surfaces 18, 19 and the longitudinal cavity 20 are formed by use of data set(s) converted from a MRI or CT scan of the patient. The remainder of the pedicle screw guide 10 shown in FIGS. 3 and 4 may be formed to meet the surgeon's particular preferences. For example, the wings 14 need only be of sufficiently length to locate the two cylindrical columns 16 in the location of the corresponding patient-matched anatomical features. The wings may take on other shapes, orientations, thicknesses, etc. without deviating from the novel aspects of this disclosure. Similarly, the medial body 12 need only be sized to accommodate the longitudinal cavity 20, and may comprise other extensions other than the wings 14 to aid in grasping or manipulating the pedicle screw guide 10 as desired.

Additionally, the wings 14 may be made from a semi-malleable or semi-rigid material to create at least a partial interference fit when the pedicle screw guide 10 is placed on the corresponding anatomical grouping for the particular surgery. For example, a snap or interference fit may be formed by subtle deflection of the wings 14 when placing the two cylindrical columns 16 adjacent the inferior articular process, and then deflect to the desired location once the wings are positioned in their final orientation. Further aspects of the disclosure in this respect are described in greater detail below.

Figure 5:
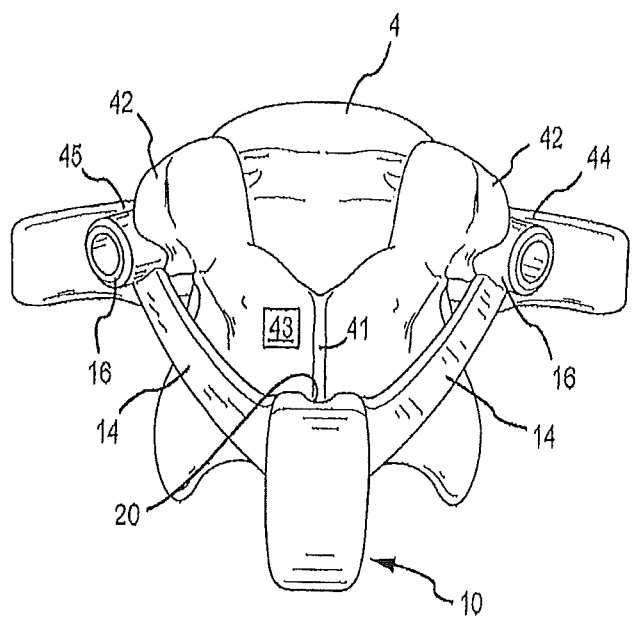

FIG. 5 is a plan view of the apparatus shown in FIG. 3 relative to a unique grouping of anatomical features according to one embodiment of the present disclosure. Here, the pedicle screw guide 10 is positioned so that the medial body 12 is centrally located above the central portion of a vertebral body 4, such that the longitudinal cavity 20 mates with the contours of the spinous process 41 for this particular vertebral body 4. Similarly, the cylindrical columns 16 are positioned one at each medial side of the pedicle screw guide 10 so that the wings 14 span the lamina 43 of the vertebral body 4 and the cylindrical columns 16 are located proximate to the inferior articular process 44, 45. The lower, patient-contacting surface 18, 19 of cylindrical columns 16 are formed to mate with the contours of the inferior articular process 44, 45 and behind the superior articular process 42.

Thus, the pedicle screw guide 10 provides a plurality of mating or matching locations, any one of which, if not positioned correctly, will impact the seating of the other two. In this aspect the pedicle screw guide provides a notable improvement over the prior art, which may be slightly rotated, misaligned or misplaced and still appear to the surgeon as if the device is properly seated. The redundancy and plurality of mating surfaces ensures that the pedicle screw guide 10 is both properly located and properly aligned. If the pedicle screw guide 10 is not properly located or aligned, the lower, patient-contacting surfaces 18, 19 will not fit on each of the inferior articular processes 44, 45 and thereby prevent the longitudinal cavity 20 from being firmly seated on the spinous process 41.

Figure 6:
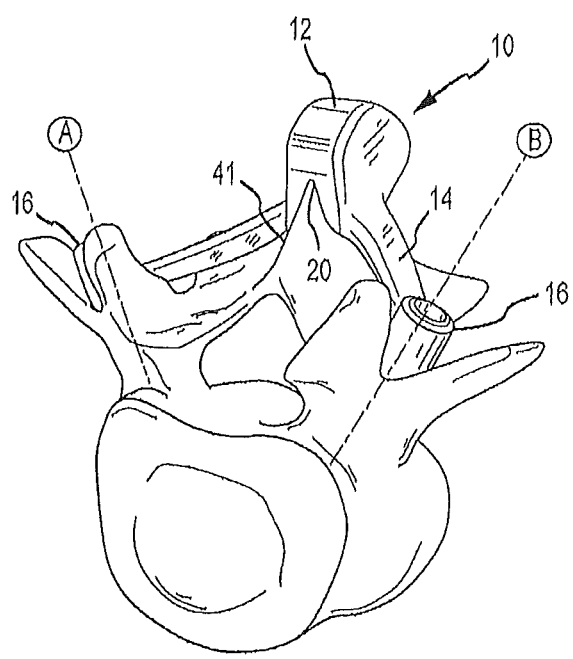

FIG. 6 is a perspective view of the apparatus shown in FIG. 5. Desired insertion trajectory lines A, B are shown to demonstrate that the locating of the cylindrical columns 16 is in addition to the orientation of the axes for each of the cylindrical columns 16, which may be independent relative to their seating adjacent the inferior articular process 44, 45 (i.e., the direction of the axis relative to normal may be different among the cylindrical columns 16). The orientation of the cylindrical columns 16 is also derived from the data set(s) described above, and in one preferred embodiment is selected based on the orientation that will permit a fixation device (i.e., pedicle screw) to be inserted consistent with the location of the pedicle and in a direction that avoids penetration of the fixation device from the pedicle (i.e., eliminates the possibility of the screw either extending through the pedicle or becoming inserted at an angle that causes the pedicle screw to exit the side of the pedicle).

Figure 7:
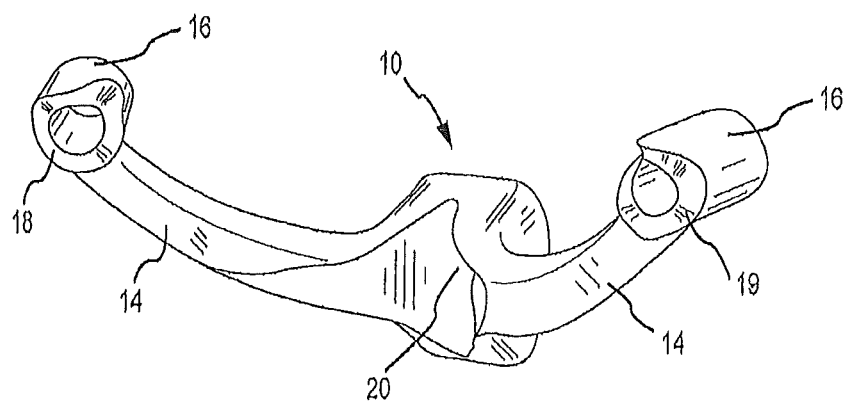

The customized or configured patient-contacting surfaces of the apparatus shown in FIGS. 3-6 are demonstrated by the bottom perspective view of the pedicle screw guide 10 in FIG. 7. Here, the lower, patient-contacting surfaces 18, 19 may comprise dynamic contours having multiple compound radii, such that the surfaces 18, 19 are completely congruent with the corresponding anatomical features of the vertebrae. Thus, the surfaces conform substantially to the surface of the vertebrae where the cylindrical columns 16 are to be located during the surgical procedure, and would not conform substantially to a different surface of the vertebrae. In this manner, the surgeon is informed immediately if the pedicle screw guide 10 is misaligned, because it will not properly seat on the vertebrae.

Figure 8:
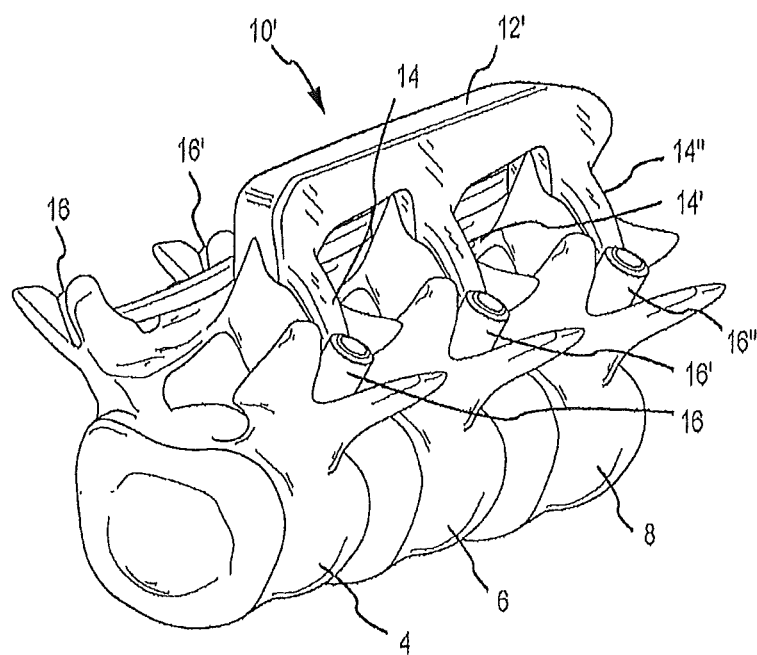

FIG. 8 shows an apparatus according to an alternative embodiment of the present disclosure. In this embodiment, a multi-level pedicle screw guide 10' is shown relative to several adjoining vertebral bodies 4, 6, 8. The multi-level pedicle screw guide 10' comprises multiple secondary wings 14' and tertiary wings 14", which each have corresponding cylindrical columns 16', 16" for inserting and aligning a plurality of pedicle screws into the adjoining vertebral sections 6, 8. It is expressly understood that multiple levels in number greater than or less than three may be achieved without departing from the spirit of the present invention.

Figure 9:
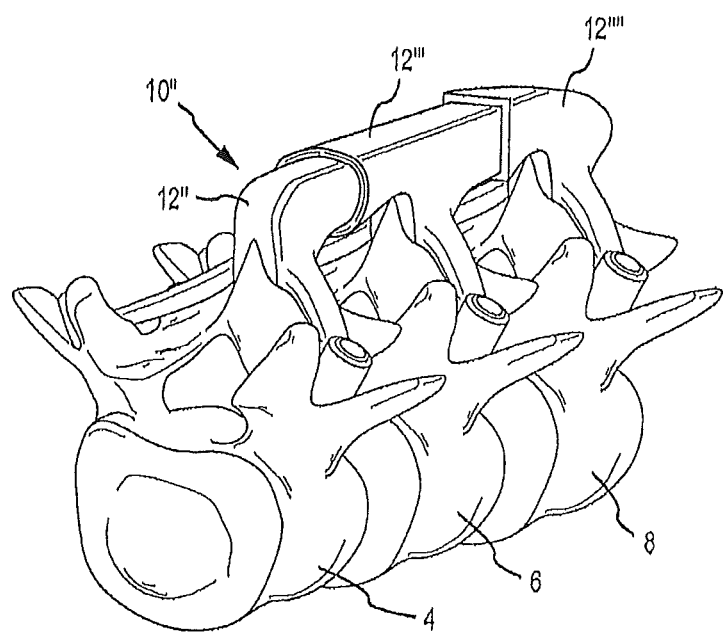

FIG. 9 shows an apparatus according to yet another alternative embodiment of the present disclosure, which is comprised of multiple sections 12", 12''', 12''''. Similar to the embodiment shown in FIG. 8, this pedicle screw guide 10" permits alignment and insertion of pedicle screws in multiple levels 4, 6, 8 of the spine. However, the multiple sections 12", 12''', 12'''' each have a modified medial body that comprises an engaging end and a receiving end, such that the multiple sections 12", 12''', 12'''' may be joined as shown in FIG. 9. The receiving and engaging ends of each of the multiple sections 12", 12''', 12'''' are different so that when assembled, only the proper ordering of the sections 12", 12''', 12'''' may be achieved (i.e., section 12" may only be joined with section 12'''). This figure demonstrates yet another aspect of the present disclosure, in particular, the ability to mate or join specific devices adjacent to one another to further ensure alignment and mating with the particular anatomical features associated with each device, as well as provide a means for applying corrective force to the vertebrae and visualize the degree of deformity correction.

Figure 10:
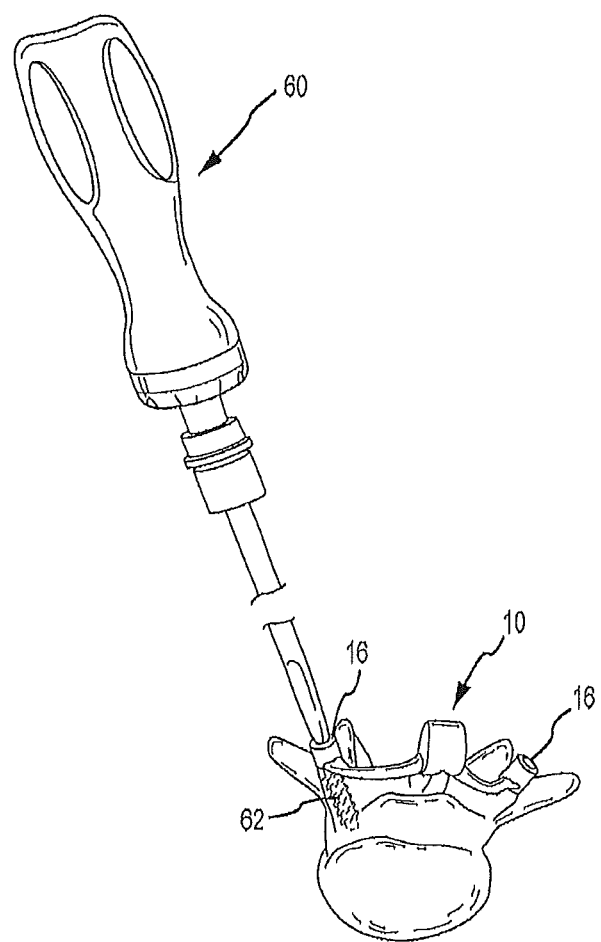

FIG. 10 shows an apparatus according to the embodiment of FIG. 5 with a customized instrument, which may be used in concert with the apparatus during a particular surgical procedure. For example, during a spinal fusion procedure such as the one described above, it is common for the surgeon to attach one or more pedicle screws to the vertebrae of the patient to achieve the desired fusion of intra-vertebral bodies. The cylindrical column 16 may have a internal diameter that corresponds with a gradually increasing external diameter of the instrument 60 such that the instrument 60 may only be advanced into the cylindrical column 16 to a predetermined distance, thereby providing a hard stop and in turn providing means for preventing the pedicle screw 62 from advancing too far into the boney anatomy of the patient. According to yet another embodiment, the hollow portion of the cylindrical column 16 may have a section with a narrower internal diameter (not shown in FIG. 10), which corresponds to a end-stop fitted to the external diameter of the instrument 60 in a manner and location to prevent the instrument from over penetrating the cylindrical column 16 and thereby inserting the pedicle screw 62 beyond a safe limit.

FIG. 11 is a perspective view of an apparatus according to yet another alternative embodiment of the present disclosure. Here, the apparatus is a pedicle screw guide 100 which further comprises a narrow bridge 112 about the medial body, which permits a collar 130 to be coupled with the modified pedicle screw guide 100, as shown in FIG. 12. The collar 130 may comprise a contoured lower surface matching the spinous process of the patient (similar to the longitudinal cavity of the embodiment shown in FIG. 3), and may be inserted into the pedicle screw guide 100 for matching the particular anatomical feature for the vertebrae operated on during the surgery. Thus, in this embodiment, the collar 130, in addition to the lower patient-contacting surfaces 118, 119 of the two cylindrical columns 116, comprises at least one of the patient-matching contours, and may be removed and replaced with other collars of differing contour as required for surgical procedures on different vertebrae. In this embodiment, the cylindrical columns 116 may further comprise one or more apertures 111 to facilitate visualization of the pedicle screw while it is being advanced into the cylindrical columns 116.

FIG. 13 is a perspective view of an apparatus for facilitating a surgical procedure according to yet another alternative embodiment of the present disclosure. In this embodiment, the apparatus formed by the system and method described above is comprised of a laminectomy cutting guide 150. This laminectomy cutting guide further comprises at least one alignment channel 151 for inserting a guide wire or other securing element, and a cutting slot 152 for directing the path of a blade or other cutting edge. As with the pedicle screw guide described in FIG. 3 above, this laminectomy cutting guide 150 also comprises a lower patient-contacting surface 155 which permits the laminectomy cutting guide 150 to mate with one or more vertebral bodies. Although shown in FIG. 13 as a generally rectangular prism, it is expressly understood that other geometrical shapes for the laminectomy cutting guide 150 are equally as practical, and considered within the scope of the disclosure.

FIG. 14 shows yet another alternative embodiment of the present disclosure. In this embodiment the apparatus formed by the system and method described above is comprised of a tube retractor 160, which also comprises a lower patient-contacting surface 165. This patient-contacting surface 165 may be formed in a section 164 of the tube retractor that is selectively removable from the cylindrical body 163 of the tube retractor 165, such that the tube retractor 165 may be reused in a number of surgeries while the section 164 is reformed and coupled to the cylindrical body 163 for each patient. The tube retractor also comprises a generally hollow inner lumen 162 and at least one tab 161 for manipulating during insertion and that assists the surgeon in ensuring proper alignment of the tube retractor 160.

FIGS. 15-17 demonstrate yet another alternative embodiment of the present disclosure. In this embodiment, the template may comprise a patient-matched guide 180 for facilitating the placement of one or more interbody devices, such as by way of example but not limitation, an implantable cage for introducing one or more bioactive substances or bone graft, or an artificial disc. In FIGS. 15 and 16, the patient-matched guide 180 is shown in one potential location relative to a unique anatomical grouping (between two adjacent vertebrae) for assisting the surgeon for placing one or more interbody devices.

In FIG. 17, the patient-matched guide 180 is shown in an exploded view to demonstrate how a plurality of components may be fabricated using the system and method described above for a particular surgical procedure. These components include a patient-specific insert 182, a guide sleeve 184 and connectors 186, which in a finally assembled state form the patient-matched guide 180 shown in FIG. 15.

Referring now in detail to FIGS. 18-19, another alternative embodiment of the present disclosure is shown. According to this embodiment, a surgical template 190 is depicted, which may further incorporate a plurality of fixation devices 198, 198', which may be used to secure the template 190 in a variety of different ways. According to this embodiment, the template 190 comprises an intermediate section 192 oriented to bridge a patient's Spinous Process, and may further comprise apertures (not shown in FIGS. 18-19) for inserting one or more fixation devices 198, 198'. The template 190 may further comprise two laterally extending portions or "wings" 194 which each terminate with a guide 196. The description of the guides provided above in connection with other embodiments disclosed herein is hereby incorporated by reference with respect to this embodiment.

According to the embodiment shown in FIGS. 18-19, fixation devices 198, 198' may be inserted through apertures (not shown) in the intermediate section 192 of the template 190 for stabilizing and securing the template 190 to the patient's Spinous Process. According to one embodiment, the direction and orientation of a first fixation device 198 is different than the orientation and direction of a second fixation device 198' to further improve the stability of the template 190 prior to insertion and placement of the permanent fixation devices. According to yet another embodiment, the apertures may be located in different locations than depicted in FIGS. 18-19, and may be fewer or greater in number according to the demands of the surgery and the patient's specific boney anatomy.

Referring now in detail to FIGS. 20-21, yet another alternative embodiment of the present disclosure is shown. In this embodiment, the template 200 further comprises two additional contacting surfaces 205 which preferably have a hollow opening at the patient-contacting end and an aperture extending therethrough for inserting a fixation device 199, 199'. As described above in connection with FIGS. 18-19, the purpose of the fixation devices 199, 199' is for securing the template 200 to the boney anatomy and facilitate securing permanent fixation devices (not shown) through a plurality of guides 206.

Referring to FIG. 20, the template 200 includes a boss 208 extending from a top surface of the template 200 for inserting a first fixation device 199, wherein the boss 208 is partially hollow to accommodate the shape and length of the fixation device 199. The boss 208 extends above a laterally extending portion or "wing" 204 of the template 200 as shown in FIG. 20. The boss 208 may extend more or less above the template than shown in FIG. 20 to provide a hard stop against over insertion of fixation device 199. Similarly, the opposite laterally extending portion or "wing" of the template 200 also comprises a boss 208' for inserting a second fixation device 199'.

Incorporating the disclosure above with respect to determining and modeling patient contacting surfaces, according to this embodiment the template 200 has at least four patient specific contacting surfaces 205, 207. This embodiment improves stability and positioning of the template, and allows a surgeon to achieve a dynamically stable surgical template, which in turn ensures that all permanent fixation devices are being positioned and inserted in a direction and orientation pre-determined for the particular surgical demands. This is accomplished by providing the four patient contacting surfaces, which act like independent legs of a table, and being positioned at different locations (and at different planes) with respect to the patient's boney anatomy to further improve the stability and positioning of the template 200.

According to the embodiment shown in FIGS. 18-21, the guides and other patient contacting surfaces may be depth-specific, and may further incorporate specific internal diameters to accommodate insertion of a temporary fixation device to a controlled depth within the patient's boney anatomy. Furthermore, the guides may have specific threaded internal surfaces to accommodate a specific fixation device and to facilitate insertion of a threaded fixation device, such as a screw. In certain embodiments, the templates could be designed for a specific patient to prevent excessive penetration of the fixation devices into the boney anatomy, or facilitate a depth-controlled first set of fixation devices to temporarily secure the templates.

According to yet another embodiment, each of the patient contacting surfaces may have an integrated blade with a patient-contacting cutting surface, integrated about at least a portion of the patient contacting surface to further set and secure the template to the boney anatomy prior to insertion of the fixation devices. The purpose of the blade is to cut through the soft tissue to achieve better template to bone contact between the template and the patient's boney anatomy. The hollow portions of the guides and other patient contacting surfaces of the template further permit soft tissue to become positioned within these hollow surfaces after the template has been set in the desired location, further securing the template to the patient's boney anatomy. The blade may be substantially cylindrical or ring shaped to match the shape of the guide, or may be oval, polygon, or other shape to match a patient contacting surface.

To add further stability to the seating and placement of the patient contacting surfaces described herein to the patient anatomy, the contacting surfaces may further comprise one or more spikes or teeth, which serve to contact and at least partially penetrate the patient anatomy to secure the device in place. In one embodiment, the spikes or teeth may be made of the same material and may be permanently attached to the patient contacting surfaces. In another embodiment, the spikes or teeth may be made of a different material, such as the ones described herein, and may further be selectively inserted onto one or more of the patient contacting surfaces as desired.

Referring now to FIG. 22, yet another alternative embodiment of the present disclosure is shown. According to this embodiment, the template 220 has a plurality of patient contacting surfaces 212, 219, which are achieved through the use of a "floating" patient-matched component 214, which may inserted into one of a plurality of guides 216 either before or after the first set of patient contacting surfaces 212 are positioned. The patient-matched component 214 may further comprise a longitudinal key 218 which corresponds to a slot or groove (not shown in FIG. 22) in the guide 216 for facilitating proper location (rotationally) of the patient-matched component 214 respective of the template 220.

Thus, according to this embodiment, the template 220 may be secured in a first position by using at least two fixation devices (not shown) securing the template 220 to its desired location, and then a plurality of patient-matched components 214 may be inserted into the guides 216 of the template 220 and seated about two distinct locations of the patient's boney anatomy.

Referring now to FIG. 23, yet another embodiment of the present disclosure is shown, wherein a instrument 240 may be used to facilitate insertion of a template 230 according to various embodiments disclosed herein. The instrument 240 is preferably comprised of a handle 242 and an extending arm 244, the length of which may vary depending on the specific patient's anatomical features and/or surgeon preferences. At the distal end of the extending arm 244 is a tab 246, which is formed to match a corresponding slot 236 located on one surface of the template 230. In operation, the instrument 240 may be joined with the template 230 and used to insert and position the template 230 within the patient's surgical site.

Referring now to FIG. 24, another alternative embodiment of the present disclosure is shown. According to this embodiment, a template 250 may be provided which is not patient specific (but in an alternate embodiment, may be patient specific) and further provides means of attaching a plurality of patient specific components 254 to the template 250. As shown in FIG. 24, the components 254 may be secured to the template 250 by aligning apertures 252, 258 and attaching one or more securing devices (not shown in FIG. 24) such as a screw, pin, or other like device. Once the components 254 are secured to the template 250, the patient contacting surfaces 262 may be used to guide and position the template 250 with the integrated components 254 in the desired location. In this manner, a standard template 250 may be provided prior to obtaining any patient data, and combined with patient specific components 254 that are formed after the patient anatomical data has been captured, thereby eliminating custom machining or fabrication of the template for a specific surgical application.

According to this embodiment the template 250 may be reusable, or in an alternative embodiment may be disposable. The template 250 may be comprised of any of the materials listed herein, but in a preferred embodiment is formed of a metal, metal alloy or a polymeric-based material. According to yet another alternative embodiment, the components 254 may snap into place or have a friction-fit connection and therefore do not require screws or other securing devices to attach to the template 250. In yet another alternative embodiment, the template 250 may be provided in a variety of set sizes and orientations to cover variability in patient anatomy and different size vertebral bodies (with respect to different levels or regions of the patient's spine).

Referring now in detail to FIG. 25, another embodiment of the present disclosure is shown. In this embodiment, the template 270 has a plurality of patient contacting surfaces 276, 278 and further comprises a plurality of clamps 272 for securing the template 270 to the Spinous Process of the patient. According to this embodiment, the clamps 272 each have a patient contacting surface 274 (here designed to contact the Spinous Process about each lateral side) to secure the template to the desired location of the patient's anatomy. Each of the clamps 272 may be positioned laterally with respect to the template 270 (shown in an elevation view) and affixed to a set position with respect to the body of the template 270. The clamps 272 may be secured in a fixed position against the Spinous Process by a number of known means, including a latch mechanism, a ratcheting mechanism, a direction-specific resistance mechanism, or a selectively-releasable tightening mechanism. In this embodiment, the clamps 272 allow oppositional forces occurring in the boney anatomy to become balanced relative to the patient's template 270. In turn, the clamping mechanism ensures and maintains the alignment of the template 270 relative to the boney surfaces further ensuring accuracy with respect to insertion of permanent fixation devices. The clamps can take a variety of shapes or embodiments including pins, paddles, or any other type of opposing surfaces that apply juxtapositional stabilizing forces.

According to one embodiment, the surgical guides depicted in FIGS. 24 and 25 may include surfaces about the patient contacting end of the guide sleeves (see 254, FIG. 24) to conform to the soft tissue existing at the facet complex where the patient contacting end of the guide sleeve contacts the patient's vertebrae (see 278, FIG. 25). Thus, according to this embodiment, the generally cylindrical guide sleeve(s) comprise a patient contacting surface that resembles a half cylinder or partial cylinder (as shown in FIGS. 24 and 25) to avoid contact with this soft tissue.

In one alternate embodiment, the surgical guide may further comprise one or more portions that have been cut-out or may selectively be cut-out or broken off to facilitate placement. One such surgical guide is shown in FIGS. 26A and 26B. According to this embodiment, the surgical guide comprises a plurality of patient contacting surfaces, one or more of which has been modified to facilitate clearance of the guide as it is being placed into position (see surfaces 282 on FIG. 26A). Furthermore, a surgical guide as described herein may comprise one or more clamping elements for securing the guide in a preferred location, such as the clamp 284 depicted in FIGS. 26A and 26B.

According to yet another embodiment, the guide sleeve(s) 254 may further permit insertion of one or more inserts 288, as shown in FIGS. 27A and 27B. These inserts 288 may be sized with external diameters for mating with the interior diameter of the guide sleeve(s) 254, and have an interior aperture running longitudinally through the insert 288 for accommodating a drill bit or tap (by way of example) of varying sizes. In practice, the insert 288 may facilitate and guide a drill bit for creating a pilot hole for further insertion of a fixation device, such as a screw. According to one embodiment, inserts 288 may further comprise one or more indicia for identifying the specific insert 288 for a particular level of a patient's spine, or other indicia indicating the direction, orientation, use or purpose of said insert 288.

Referring now to FIG. 28, the inserts 288 provided with the surgical guides for mating with the guide sleeves 254 may have a varying length L, and may be made longer or shorter depending on the geometry of the guides, the patient's anatomy, the purpose of the insert, etc. For example, if a greater depth of a particular drill is required, the insert 288 may be shorter to accommodate further penetration of the drill bit into the patient's vertebrae. Likewise, the interior aperture of the insert 288 may have varying diameter depending on the precise tool or instrument that is intended to be used with the insert (as depicted in FIGS. 29A and 29B). In this manner, a surgeon may insure that he or she is using the proper tool, such as a drill or tap, with each of the inserts (which may further include one or more indicia to indicate the location or specific use intended for said insert) when performing a surgical procedure. Further illustration of the principles described above see FIGS. 29A and 29B, which depict an insert with a 4.5 millimeter aperture diameter for placement of a tap instrument and a ⅛ inch aperture diameter for use in connection with a ⅛ inch drill bit, respectively.

Referring now to FIG. 30, according to one embodiment the inserts 288 described above may also include patient specific contacting surfaces 294, for further matching the insert 288, in addition to the guide sleeves 254, with the patient specific anatomy. This allows greater stability and positioning of the insert 288, and the guide with the insert 288 included, in the proper location. In addition, for inserts 288 used in connection with a drill bit or other vibrating or oscillating tool, these patient matching surfaces 294 on the insert 288 would also prevent the distal end of the drill bit from "walking" or moving on the surface of the vertebral body when creating the initial pilot hole, thereby reducing the risk of incorrect trajectory of a fixation device.

According to further embodiments of the present disclosure, the patient contacting surfaces, formed by one or more protrusions extending from the main body of the surgical guide described in greater detail above (and according to several embodiments disclosed herein) may comprise a sharp or semi-sharp contacting edge for penetrating and affixing to the soft tissue surrounding the patient's anatomical feature, such as a facet joint. The contacting surfaces may, according to this embodiment, comprise recessed cavities for soft tissue incursion. These recessed cavities create edges around the outside of the legs, which could be sharp or selectively sharpened to facilitate cutting through soft tissue to rest/mate with underlying bone. This is particularly important for spinal surgical procedures where the precise location of the patient contacting surface must be within a small degree of error, and must remain permanent throughout the procedure.

Referring now in detail to FIG. 31, the insert may further comprise a key or notch 296 about one surface of the generally cylindrical body of the insert, which is configured to mate with a cutout or slot 298 on the guide sleeve 254 of the device. In this manner, the proper rotation/orientation of the insert 288 is insured when guiding the insert into the hollow body of the guide sleeve 254.

Referring now to FIGS. 32A-34B, further illustrations of a cutting guide (such as the one depicted in FIG. 13 above), are provided. According to one embodiment, the cutting guide comprises a plurality of patient specific contacting surfaces 302 about at least one surface of the cutting guide. The cutting guide further comprises, in a preferred embodiment, a patient specific "track" 303 for facilitating insertion of a cutting instrument (as shown in FIGS. 33A-C) and controlling the depth of insertion for that instrument to prevent unnecessary cutting of the underlying surface during a particular surgical procedure by further providing one or more instrument contacting surfaces 304. According to the embodiment shown in connection with FIGS. 32A-34B, the cutting guide may be provided for a laminectomy. According to other embodiments, the patient-specific guide may be fabricated for use in performing a corpectomy, a Pedicle Subtraction Osteotomy (PSO), a Smith-Peterson Osteotomy (SPO), a Vertebral Column Resection (VCR), or an Asymmetric Osteotomy (in either the sagittal or coronal plane), among others.

These patient-specific cutting guides may be fabricated from patient anatomical data, and may assist in performing complex procedures with greater certainty in their outcomes. For example, certain osteotomies, specifically PSO and SPO, require a great deal of surgical skill and are often time consuming. This is due in part to the intimate relationship of the vascular and neural elements to the boney structures, which create navigational challenges for a surgeon to safely and efficiently resect the bone during one of these procedures. This is especially true from a posterior approach. By using a patient-specific guide, a surgeon may confirm positioning and alignment of the cutting trajectory and path prior to initiating the procedure, and in furtherance of the disclosure provided above in relation to FIGS. 32A-34B, may also provide a degree of depth control essential for avoiding contact with vascular and neural elements.

In one embodiment, the cutting tool associated with the cutting guide shown in FIGS. 32A-34B is typical of the type of tools currently used in surgical procedures today. According to another embodiment, a specialty cutting bur or tip may be included with the instrument to facilitate further control of the location and depth of the instrument, as described in further detail below. For example, as shown in FIGS. 33A-33C, the cutting portion of the instrument may have a track ball 308 that prevents greater insertion of the instrument into the cutting guide than required for the patient specific procedure.

As shown in greater detail in FIGS. 34A-34B, the track ball 308 may be inserted into a first portion of the "track" 303 of the cutting guide, but not permitted to insert a second or deeper portion of the "track" of a cutting guide (through which the cutting surface is permitted to travel), thereby insuring proper depth of the cutting instrument. Further geometrical configurations other than those shown in FIGS. 34A-34B may be provided that allow the track ball 308 to move horizontally with respect to the top surface of the cutting guide, and in some instances laterally and downwardly into the track 303 of the cutting guide. In this embodiment, the cutting instrument would therefore be permitted to move at a certain depth about a patient's anatomy in a certain location of the "track" 303 of the cutting guide, but achieve a greater depth at yet other locations about the "track" 303 of the cutting guide. Thus, the depth permitted with respect to the instrument relative to the cutting guide may be variable about the "track" 303 of the cutting guide.

Other benefits achieved from the use of these patient-specific cutting guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

FIG. 35 is a top plan view according to yet another alternative embodiment of the present disclosure. In this embodiment, the device 310 may provide one or more patient contacting elements comprising break-away portions 314, which allow for placement of a fixation device (such as a pedicle screw) without detaching the device from the patient's boney anatomy. The break-away lateral edged may be formed by creating slots 315 in the surfaces of the surgical guide portions of the device, which provide perforation axes for the portions 314 to be broken.

According to this embodiment, the guide sleeve may be asymmetric, which would permit two different inner diameters: one that facilitates guidance of the hand tools (i.e. drill, tap) and one that accommodates the boss or cap of the device (such as the tulip of the pedicle screw). Once the break-away portion 314 of the guide sleeve is removed, a clear view and path to the vertebra is possible and allows pedicle screw placement without removing the guidance device.

FIG. 36 is a detailed view of the device according to the embodiment shown in FIG. 35. In FIG. 36, a detailed view of the slots 315 are shown, which in a preferred embodiment may be formed during the fabrication of the device 310, but in alternate embodiments may be formed after the device has been fabricated by perforation or other techniques for creating a slot 315 about a certain surface of the guide sleeve of the device 310.

FIGS. 37-39 are additional views of the device according to the embodiment shown and described in relation to FIG. 35. In FIG. 37, the asymmetrical guide sleeve is shown with the two break-away portions 314 separated from the device 310. In FIG. 38, the embodiment shown and described in relation to FIGS. 26A-B is shown, but now having an asymmetrical guide sleeve with break-away portions 314 as described above.

FIGS. 40A-D are additional perspective views of the devices described above in relation to FIGS. 35-39, according to the embodiments having at least one or more break-away portions. Once removed, the break-away portions are preferably disposed by the surgeon.

Each of the embodiments described herein may be provided in a modular (i.e., single level) or a monolithic (i.e., multilevel) configuration. Thus, for ease of facilitating the description provided herein, certain embodiments have been shown in one (modular or monolithic) embodiment, but may be provided in a different (monolithic or modular) configuration without departing from the spirit of the disclosure. In various aspects, the monolithic embodiments may comprise anywhere from two to ten levels with respect to vertebral bodies, or enclose multiple locations of a patient's boney anatomy other than the spine. It is expressly understood that the embodiments described herein are for the purpose of illustrating certain embodiments of the disclosure, and are not intended to be limiting with respect to the scope of the disclosure.

According to the various embodiments described herein, a variety of fixation devices may be quickly and easily fabricated for use in a surgical or educational setting, including but not limited to pins, screws, hooks, clamps, rods, plates, spacers, wedges, implants, etc. Similarly, a variety of instruments and/or other devices may be fabricated based on patient specific data, including but not limited to patient-matched inserters, scrapers, cutters, elevators, curettes, ronguers, probes, screwdrivers, paddles, ratcheting mechanisms, removal and rescue tools, cannula, surgical mesh, etc.

Included among the apparatus that may be fabricated using patient-specific data and including a plurality of patient-matched surfaces are devices used as implants, including numerous implants used to restore disc space height in a patient's vertebrae. For example, a variety of patient matched metallic, polymeric or elastomeric implants may be fabricated using the methods described herein, where certain patient contacting surfaces of the implant accurately and precisely match the anatomy of the patient. In one embodiment, the implant may be matched to an anatomic feature of a patient that has degenerated and needs to be restored. In another embodiment, the implant may be necessary to correct structural or physiological deformities present in the patient anatomy, and thereby serve to correct position or alignment of the patient anatomy. Other implants may be patient specific but do not serve a restorative or other structural function (i.e., a hearing aid implant casing).

The implants described herein may be manufactured via additive manufacturing. In the context of spinal implants, the implants may be used in all approaches (anterior, direct lateral, transforaminal, posterior, posterior lateral, direct lateral posterior, etc). Specific features of the implant can address certain surgical objectives, for example restoring lordosis, restoring disc height, restoring sagittal or coronal balance, etc.

Other applications contemplated by the present disclosure include interbody fusion implants, disc space height restoration implants, implants having footprint matching, surface area maximization, shape and contour matching to endplates or other vertebral defects, and may further specify the contact surface such as the relative degree of roughness or other surface features. For example, an implant may be fabricated based on the patient anatomy which further comprises a direction-specific shape, such that the implant may fit through an access portal and into the disc space without difficulty. Alternatively, the implant may be fabricated in a manner to account for anatomic constraints both at the point of implant and through the path the implant must travel, and may further compensate for anatomical defects. In the context of a spinal implant, the implant may further specify a desired angle of lordosis or coronal defect correction, specify a patient specific height of the implant or (desired height following disc height restoration), specify a degree of expansion permitted (for expandable implants), and may be unidirectional or multi-directional depending on the surgery and the surgeon preference.

According to one embodiment, the fabrication of a patient-matched device may be used to create patient-matched vertebral plates. By way of example but not limitation, patient data may be obtained to create matching surfaces of one or more anterior cervical or lumbar plates used for spinal reconstructive surgeries. Plates may comprise contours or surface features that match boney anatomy, including matching surfaces spanning more than one segment or vertebrae. In yet another embodiment, the patient data may be used to create specific patient matched plates with identifiers for the location of the plate, and may further comprise custom drill holes or other alignment points specific to the patient. Other types of plates, besides those utilized in spinal surgery and described, may incorporate patient matching features described herein without departing from the present disclosure.

According to another embodiment of the disclosure, an apparatus is provided with the ability to monitor one or more biosignals during a procedure using apparatus described herein. In a preferred embodiment, the biosignals obtained from a patient contain at least an Electromyography (EMG) component, which can be measured and observed during at least a portion of the surgical procedure. In alternate embodiments, the system comprises a somatosensory evoked potential (SSEP) component and/or a motor evoked potential (MEP) component. Other neural monitoring modalities are also contemplated for use with this embodiment. An analysis of the biosignals may be carried out to determine whether a fixation device or instrument, such as a drill tip, has been properly placed, or alternatively if the device or instrument has made contact with neural elements present near the surgical site.

According to this embodiment, one or more devices or instruments may be in communication with a monitoring apparatus, which receives and reports EMG signal data from a patient via a measurement channel from the device or instrument. The monitoring apparatus preferably obtains the data and presents it to a user in a graphical or other visual form. Based on the presentation of data obtained from the monitoring apparatus, the surgeon can determine whether the final placement of a device or instrument is received in the patient's boney anatomy or in the muscular tissue or has come into contact with neural elements, for example.

In practice, one or more devices or instruments may incorporate an EMG sensor, such as an electrode, which is in communication with at least one measurement channel, which in turn provides EMG data to the monitoring apparatus. The monitoring apparatus then displays the data received from the EMG sensor(s), and preferably permits the surgeon or other medical professional to compare the value associated with the EMG data with predetermined EMG data, including EMG data associated with different types of tissue. In a preferred embodiment, the predetermined EMG data includes at least data associated with a muscular region, a neural region, a vascular region and a boney region of the patient's anatomy. By making the comparison of the measured EMG data to the predetermined EMG data, the surgeon or other medical professional may determine whether the EMG sensor has sensed a particular tissue type, which in turn guides the placement of the device or instrument with which the EMG sensor is associated with.

Referring now to FIGS. 41A-C and 42A-B, various embodiments of the intraoperative monitoring (IOM) enabled devices and instruments are depicted. In reference to FIG. 41A, this embodiment comprises an instrument, such as a drill, which further comprises a conductive drill bit 324. The drill bit 324 may be inserted into a conductive drill sleeve 326, the drill sleeve 326 in electrical communication 330 with a power controller (not shown in FIG. 41A). The relationship between the drill bit 324 and the drill sleeve 326 is such that the two have a close tolerance 333, ensuring substantially constant contact between the length of the drill bit 324 and the drill sleeve 326. The drill sleeve 326 may further be inserted and secured within a guide sleeve 354, which in turn may by secured to a surgical guide device 410.

Referring now to FIG. 41B, once assembled, the drill bit 324 and drill sleeve 326 are inserted into the guide sleeve 354, and the drill bit 324 extends through the guide sleeve 354 to permit contact with the patient anatomy. In one embodiment, the drill bit may penetrate a patient's pedicle located on the patient's vertebrae. In a preferred embodiment, the drill bit 324 further comprises a generally cylindrical stopper which abuts a plate located on the distal end of the drill sleeve 326 (as shown in FIG. 41B). This connection provides a secure connection and prevents the penetration of the drill bit 324 further than permissible for a particular surgical application. This connection also ensures a high fidelity electrical channel through the communication from the power controller (not shown) to the conductive drill sleeve 326 and thereby to the drill bit 324. In this manner, electrical signals (preferably EMG) may be evoked from the drill bit during the surgical procedure and transmitted to one or more monitoring apparatus (not shown). An alternate view of the assembly is depicted in FIG. 41C.

In yet another embodiment, the guide sleeve 354 may evoke EMG signals, as in the embodiment shown in FIGS. 42A-B. According to this embodiment, the guide sleeve 354 is embedded with one or more electrodes 332, which are in communication 330 with a power controller (not shown), thereby providing intraoperative monitoring. In this embodiment, the electrode(s) 332 are embedded into the guide sleeve(s) 354 to provide electrical communication with a conductive drill sleeve 336 or other conductive element placed in contact with the electrode(s) of the guide sleeve 354. For example, the electrode(s) may contact other conductive elements, such as a tap instrument or a fixation device, such as a screw. These conductive elements are in electrical communication with the power controller and one or more monitoring apparatus (not shown) to permit the surgeon or other medical professional to compare the EMG data obtained from the conductive elements with predetermined EMG data for different tissue types. This enables the surgical devices, instruments and guides described herein to be IOM enabled and provide monitoring of the placement of various inserts, fixation devices or other conductive elements during the surgical procedure.

According to yet another embodiment, devices and guides for improving sacral fixation is disclosed. In this embodiment, a device or guide is fabricated from patient data which includes one or more trajectories that cause a fixation device to enter a disc space (as opposed to entering a pedicle), and in a preferred embodiment may include trajectories to permit the fixation device to intersect one or more implants, including but not limited to an interbody fusion device. In a preferred embodiment, sacral fixation occurs by providing trajectories in one or more surgical guides, the trajectories located generally in the region of the end plates and sacral (S1) promontory. Via these trajectories, placement of a pair of pedicle bone screw anchors in the pedicles extending to the sacral promontory, preferably in conjunction with an interbody implant is achievable. In a preferred embodiment, both the guide(s) for ensuring the trajectories of the sacral fixation devices and the interbody implant are formed using the methods described herein.

According to this embodiment, the patient specific spinal implant and associated fixation devices offer a significant improvement in implant design. In the disclosed design, an interbody fusion device may be placed from a bilateral PLIF or a unilateral TLIF approach, and may further become mechanically interlocked with a vertebral anchoring or fixation device. The fixation device may be, by way of example but not limitation, a modified vertebral pedicle screw. The surgical guide may be fabricated using patient data to provide a predictable and reproducible trajectory, and to ensure that the fixation devices inserted through the guide interlock with the interbody fusion device. While this patient matched implant has been described for use in the lumbosacral joint (L5 S1), this embodiment may also be used for all other levels of the cervical, thoracic, and lumbar spine.

In order to maintain the appropriate spatial relationship between spacer and screw, a patient matching guide may also register the location of the fixation device and a spacer, and provide the appropriate convergent and sagittal pedicle screw angle without perforating the medial cortex and entering the spinal canal. In a preferred embodiment, a plastic or combination material (i.e., metal frame with patient matched plastic inserts) patient specific device could provide these desired trajectories.

The apparatus described herein may be used in a minimally invasive setting, and may further comprise a number of interlocking modules which may be assembled after delivery through a cannula or other minimally invasive passageway to the surgical site. Alternatively, one or more portions of an apparatus may be nested within another portion of the apparatus, or alternatively nested within an instrument or other device that is used to deliver the apparatus through a cannula or other minimally invasive portal. In accordance with the manufacturing modalities described above, the apparatus may be fabricated with specific matching surfaces, which only permit assembly in the correct manner, and may further comprise indicia or other means of indicating which portions nest within other portions or which modules adjoin other modules of the apparatus.

For example, in one embodiment it is contemplated to provide multiple nested patient-matched guides, whereby at least one but potential several modules are assembled to create a "base guide." This base guide may span several spinal segments of a patient, and may be secured to the vertebrae by one or more anchors. The one or more anchors may include, but are not necessarily limited to, a pedicle screw fixation device used in the final construct. Once the base guide has been secured in the proper location (by aligning, for example, the patient-matching surfaces with their corresponding boney anatomy), additional guides may be introduced and "nest" onto the base guide. In one embodiment, these additional guides may include cutting/drilling/routing guides. In another embodiment, the additional guides may include fixation device trajectory guides. In yet another embodiment, the additional guides may include disc space restoration guides or implant insertion guides.

According to the embodiment where the additional guides include at least one cutting/drilling/routing guide, the surgeon may then introduce one or more sequential nested guides onto the base guide, which are designed to have surfaces conforming with the completed cut/drilled/routed boney anatomical surface (i.e., which adapt to areas of recently resected bone, thereby allowing sequential cuts to be made deeper and deeper into the bone anatomy, or allowing final placement of fixation devices adjacent the area of the cuts). In this manner, embodiments described herein may be used in combination to achieve an even more reliable outcome by ensuring reliable cuts (and reliable deformity correction) using a first guide prior to providing a second or subsequent guide(s) for inserting a fixation device in a reliable trajectory.

According to an embodiment where a surgical guide is prepared to assist in a cutting operation, the guide may comprise a plurality of cutting planes such that the use of a cutting instrument through the plurality of cutting planes provides a measured and exact cut through a boney anatomical structure. Accordingly, one or more cutting guides fabricated by the methods described herein will result in a measured and exact correction of an anatomical deformity by cutting through the plurality of cutting planes and subsequently removing the boney anatomy that has been cut using the one or more cutting guides. In the context of a spinal surgical procedure, the cutting guides may be used in different areas of the spine or in different levels of the patient's vertebrae to correct complex deformities.

The apparatus disclosed herein may be made of a variety of different materials. These materials may include, by way of example but not limitation, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials. According to one embodiment, the apparatus may be made from a first material that is used to plan or demonstrate the surgical procedure, prior to making the apparatus in a second material for use during the surgical procedure. In this manner, a surgeon or other medical professional may use a mock-up of a guide and/or the mapped patient anatomical features (manufactured of a first material) prior to performing the surgery with apparatus prepared based on the patient data and/or the surgical planning process facilitated by the mock-up guide and any other mock-up of the patient anatomy. By way of example but not limitation, this use of a first set of apparatus may be used to practice techniques to be employed during the surgical procedure or otherwise allow the surgeon to perform a "dry run" of the procedure. The ability to practice also provides an opportunity for the surgeon to visualize and confirm the fit of various instruments and fixation devices with the mock-up guides or other apparatus. Furthermore, these mock-ups may provide an inexpensive way for the surgeon to educate other medical professionals or the patient prior to the surgical procedure.

Referring now to FIG. 43, a method according to one alternate embodiment of the present disclosure is described. According to this method, one or more of the following steps may be followed to prepare a patient-matched device, guide or implant. First, a surgeon receives information that indicates a benefit of having a patient matched technology employed 510. Second, the patient is scanned to capture the data associated with anatomical features which are suitable for three dimensional rendering 512. Next, the surgeon reviews the data 514 and prepares an initial surgical plan 516. Then, the image data captured from the patient scan is transferred to an engineering team 518 or other medical professionals for processing 520. During processing, the patient data is used to create an accurate anatomical zone surrounding the surgical site of operation. During this process, the data may be converted to create an anatomical file 522. The next step is to prepare a surgical plan using the three dimensional anatomical zone data to locate one or more areas of interest 524, which in turn provide the surgeon with one or more patient matching surfaces and one or more trajectories. Then the surgeon modifies and approves the surgical plan 526 and the design of the patient matched devices, guides and instruments 528 commences for the finished plan. After the design stage, the manufacture of the devices 530 occurs, and once verified are supplied to the operating location 532. The remaining steps of sterilization 534 and using the patient matched devices during the surgery 536 are carried out at the time of surgery. It is to be expressly understood that fewer than all of the foregoing steps may be followed without deviating from the spirit of the present disclosure.

It is also to be expressly understood that, although rapid prototyping and associated manufacturing techniques (such as CNC) have been used in illustrating the present disclosure, it is contemplated that other manufacturing modalities could be employed without sacrificing the benefits of the present disclosure. For example, processes not associated with additive manufacturing may be utilized, as may alternate imaging techniques, to fabricate a custom device, guide or instrument using the steps described herein.

Furthermore, the present disclosure may also be advantageous in light of recent improvements in decentralized manufacturing. For example, devices, guides and instruments may soon be capable of fabrication in a number of different and convenient settings, including but not limited to an off-site manufacturing location, an on-site manufacturing location, using equipment present in a surgeon's clinic or offices or in a public or private hospital. In this manner, the patient data and the process of obtaining an accurate and matching device, guide or instrument may be facilitated by the proximity of the manufacturing processes, and is considered within the scope of the present disclosure.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A patient-specific pedicle screw guide that mates with the anatomical features of a particular vertebra, comprising:
    a medial body configured to be positioned adjacent a vertebra;
    a first elongated wing extending from a first side of the medial body and terminating with a first column, wherein the first column comprises a first lower surfaces that anatomically mates with at least one first contour of the particular vertebra; and
    a second elongated wing extending from a second side of the medial body opposite the first side and terminating with a second column, wherein the second column comprises a second lower surface that anatomically mates with at least one second contour of the particular vertebra; and wherein the first and second lower surfaces are determined from and complementary to the patient's anatomy.

2. The patient-specific pedicle screw guide according to claim 1 further comprising at least one leg extending from an inferior side of the medial body, wherein the at least one leg comprises a lower surface that anatomically mates with at least one contour of the particular vertebrae.

3. The patient-specific pedicle screw guide according to claim 2, wherein the guide is configured to span multiple vertebrae of the patient.

4. The patient-specific pedicle screw guide according to claim 3, wherein the guide may be coupled to a plurality of additional guides for spanning multiple vertebrae of the patient.

5. The patient-specific pedicle screw guide according to claim 3, wherein the guide is comprised of a plurality of guides that may be arranged in a monolithic or multi-level configuration for spanning multiple vertebrae of the patient.

6. The patient-specific pedicle screw guide according to claim 1, wherein the first and second column define pathways for guiding at least one instrument.

7. The patient-specific pedicle screw guide according to claim 2, wherein the lower surface of the at least one leg anatomically mates with at least one contour of the lamina or inferior articular process of the particular vertebrae.

8. The surgical guide according to claim 2, wherein the lower surfaces of the at least one legs each anatomically mate with at least one contour of the lamina or inferior articular process of one or more vertebrae.

9. The patient-specific pedicle screw guide according to claim 1, further comprising a first and second bore extending longitudinally through the first and second columns.

10. The patient-specific pedicle screw guide according to claim 9 wherein the first and second bores are oriented along pre-determined trajectories for placing one or more implants into the particular vertebrae, and wherein the pre-determined trajectories are determined from the anatomical features of the patient.

11. The surgical guide according to claim 9 wherein the first and second bores are oriented along pre-determined trajectories for inserting one or more implants, and wherein the pre-determined trajectories are determined from the anatomical features of the patient.

12. The surgical guide according to claim 1, wherein the guide is configured to be used on one or more vertebrae of the patient.

13. The surgical guide according to claim 1, wherein the guide may be coupled to a plurality of additional guides for spanning multiple anatomical features associated with the patient.

14. The surgical guide according to claim 1, wherein the guide is comprised of a plurality of guides that may be arranged in a monolithic or multi-level configuration for spanning multiple anatomical features associated with the patient.

15. The surgical guide according to claim 1 wherein the guide is comprised of at least a first section and at least a second section, which are selectively interconnected to one another in a position of use.

16. The surgical guide according to claim 15 wherein the at least a first and second section are selectively interconnected about the medial body of the surgical guide.

* * * * *